(12) United States Patent
Yen et al.

(10) Patent No.: US 10,186,668 B2
(45) Date of Patent: Jan. 22, 2019

(54) ORGANIC ELECTROLUMINESCENT MATERIAL AND USE THEREOF

(71) Applicants: Feng-Wen Yen, Taipei (TW); Cheng-Hao Chang, Miaoli (TW)

(72) Inventors: Feng-Wen Yen, Taipei (TW); Cheng-Hao Chang, Miaoli (TW)

( * ) Notice: Subject to any disclaimer, the term of this patent is extended or adjusted under 35 U.S.C. 154(b) by 87 days.

(21) Appl. No.: 15/449,918

(22) Filed: Mar. 4, 2017

(65) Prior Publication Data
US 2018/0254415 A1   Sep. 6, 2018

(51) Int. Cl.
*H01L 51/00*   (2006.01)
*C09K 11/06*   (2006.01)
(Continued)

(52) U.S. Cl.
CPC ........ *H01L 51/0072* (2013.01); *C07D 487/04* (2013.01); *C09K 11/025* (2013.01);
(Continued)

(58) Field of Classification Search
None
See application file for complete search history.

(56) References Cited

U.S. PATENT DOCUMENTS 8,062,769 B2   1/2011   Komori et al.
8,013,330 B2   9/2011   Komori et al.
(Continued)

FOREIGN PATENT DOCUMENTS

WO   2014204464 A1   12/2014

*Primary Examiner* — Jay Yang

(57) ABSTRACT

There is provided a novel material of formula(1) or formula (2) and the organic EL device employing the novel material as phosphorescent light emitting host of emitting layer, delayed fluorescence dopant of emitting layer, and hole blocking layer can display good performance like as lower driving voltage, power consumption, increasing efficiency and life time.

formula(1)

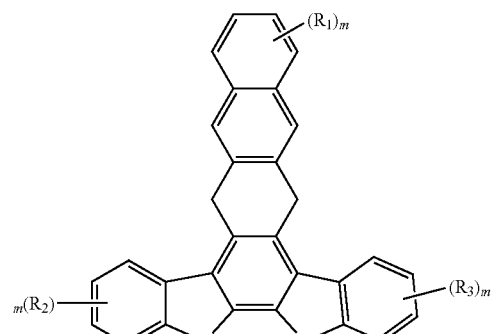

formula(2)

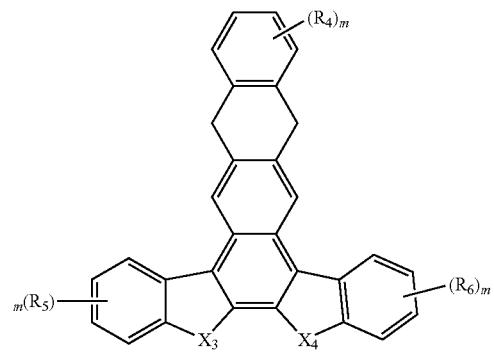

wherein m, $X_1$ to $X_4$ and $R_1$ to $R_6$ are the same definition as described in the present invention.

14 Claims, 1 Drawing Sheet

| 14 | — metal electrode |
| 13 | — electron injection layer |
| 12 | — electron transport layer |
| 11 | — hole blocking layer |
| 10 | — emitting layer |
| 9  | — electron blocking layer |
| 8  | — hole transport layer |
| 7  | — hole injection layer |
| 6  | — transparent electrode |

(51) Int. Cl.
   *C09K 11/02* (2006.01)
   *C07D 487/04* (2006.01)
   *H01L 51/50* (2006.01)

(52) U.S. Cl.
   CPC .......... *C09K 11/06* (2013.01); *H01L 51/0067* (2013.01); *C09K 2211/1007* (2013.01); *C09K 2211/1059* (2013.01); *H01L 51/5012* (2013.01); *H01L 51/5016* (2013.01); *H01L 51/5072* (2013.01); *H01L 51/5096* (2013.01); *H01L 2251/5384* (2013.01)

(56) References Cited

U.S. PATENT DOCUMENTS

| | | |
|---|---|---|
| 7,993,760 B2 | 11/2011 | Kai et al. |
| 2013/0126856 A1 | 3/2013 | Yokoyama et al. |
| 2013/0240796 A1 | 9/2013 | Parham et al. |
| 2015/0105563 A1 | 4/2015 | Ahn et al. |
| 2016/0260909 A1 | 9/2016 | Dyatkin et al. |

| 14 | — metal electrode |
| 13 | — electron injection layer |
| 12 | — electron transport layer |
| 11 | — hole blocking layer |
| 10 | — emitting layer |
| 9 | — electron blocking layer |
| 8 | — hole transport layer |
| 7 | — hole injection layer |
| 6 | — transparent electrode |

ORGANIC ELECTROLUMINESCENT MATERIAL AND USE THEREOF

FIELD OF INVENTION

There is provided a material for organic electroluminescence (herein referred to as organic EL) device having general formula(1) or formula(2), an organic EL device employing the material as phosphorescent emitting host, delayed fluorescent dopant, and hole blocking layer (HBL).

BACKGROUND OF THE INVENTION

An organic EL device is composed of layers of organic materials situated between two electrodes, which include a hole transporting layer (HTL), an emitting layer (EML) and an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT (metal to ligand charge transfer) state of organic metallic complexes.

Recently, a new type of fluorescent organic EL incorporating mechanism of thermally activated delayed fluorescence (TADF) has been developed by Adachi and coworkers is a promising way to obtain a high efficiency of exciton formation by converting spin-forbidden triplet excitons up to the singlet level by the mechanism of reverse intersystem crossing (RISC) by using a material having a small energy gap between the singlet level and the triplet level. However, further improvement in luminous efficiency of the organic EL device in a high current density region is still desired.

The phosphorescent organic EL utilizes both triplet and singlet excitons. Cause of longer lifetime and the diffusion length of triplet excitons compared to those of singlet excitons, the phosphorescent organic EL generally need an additional hole-blocking layer (HBL) between the emitting layer (EML) and the electron transporting layer (ETL) or the electron transporting layer with hole blocking ability instead of typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO (highest occupied molecular orbital) and LUMO (lowest unoccupied molecular orbital) energy levels suitable to block hole transport from the EML to the ETL and to pass electrons from the ETL to the EML, in addition, the good thermal and electrochemical stability of the materials are also needed.

For full-colored flat panel displays in AMOLED or OLED lighting panel the material used for the phosphorescent dopant for emitting layer are still unsatisfactory in half-life time, efficiency and driving voltage. These organic metallic complexes still have disadvantages for industrial practice use. The phosphorescent dopant with preferential in-plane (horizontal) emitting dipoles are beneficial to optical out-coupling of OLED, since the ratio of vertical emitting dipoles contributing little to external emission is reduced and the radiation pattern of a horizontal emitting dipole is in general more suitable for optical out-coupling. Therefore, an emitter with proper substituents can be helpful to enhance the ratio of horizontal emitting dipole in the emission layer of OLED. Meanwhile, the proper substituents around an emitter can effectively block nearby electrons and holes, so that electrons and holes can easily recombine in the emitter and the efficiency of OLED can be improved.

There continues to be a need for organic EL materials which is able to efficiently transport electrons or holes and block holes, with good thermal stability and more efficient EML materials for high emitting efficiency. According to the reasons described above, the present invention has the objective of resolving such problems of the prior-art and offering a light emitting device which is excellent in its thermal stability, high luminance efficiency, high luminance and long half-life time. The present invention disclose a novel material having general formula(1) or formula(2), used as phosphorescent emitting host, delayed fluorescent dopant, and hole blocking layer (HBL) have good charge carrier mobility and excellent operational durability can lower driving voltage and power consumption, increasing efficiency and half-life time of organic EL device.

SUMMARY OF THE INVENTION

A novel material can use as phosphorescent emitting host, delayed fluorescent dopant and hole blocking layer (HBL) for organic EL and their use for organic EL device are provided. The material can overcome the drawbacks of the conventional materials like as shorter half-life time, lower efficiency and higher power consumption.

An object of the present invention is to provide the novel material which can be used as hole blocking layer (HBL) material for organic EL device and can efficiently confine excitons to transfer to electron transport layer.

An object of the present invention is to provide the novel material which can be used as phosphorescent host material, delayed fluorescent dopant of emitting layer for organic EL device and increase the efficiency and half-life time.

The present invention has the economic advantages for industrial practice. Accordingly the present invention, the material which can be used for organic EL device is disclosed. The mentioned the material is represented by the following formula(1) or formula(2):

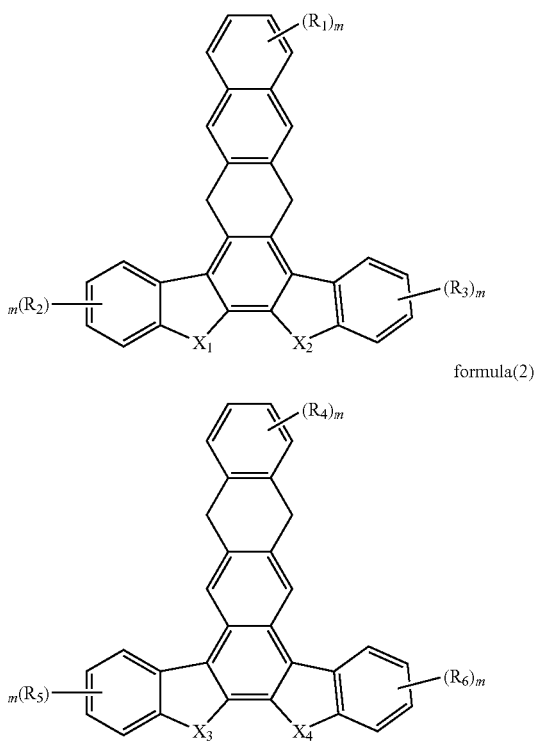

formula(1)

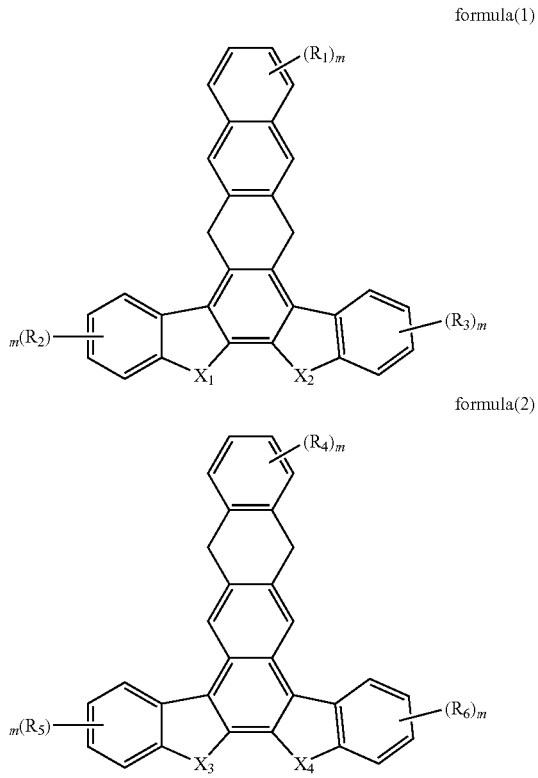

formula(2)

wherein m represents an integer of 0 to 4, $X_1$ to $X_4$ independently represent a divalent bridge selected from the atom or group consisting from O, S, $C(R_7)(R_8)$, $N(Ar)$, $Si(R_9)(R_{10})$, Ar is selected from the group consisting of a hydrogen, a substituted or unsubstituted aryl group having 6 to 60 carbon atoms or a substituted or unsubstituted heteroaryl group having 3 to 60 carbon atoms, and provided that Ar represents a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted quinoline group, a substituted or unsubstituted isoquinoline group, a substituted or unsubstituted quinazoline group, a substituted or unsubstituted phenanthroline group, a substituted or unsubstituted dihydroacridine group, a substituted or unsubstituted phenothiazine group, a substituted or unsubstituted phenoxazine group, and a substituted or unsubstituted dihydrophenazine group; $R_1$ to $R_{10}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

BRIEF DESCRIPTION OF THE DRAWINGS

The FIGURE shows one example of organic EL device in the present invention. 6 is transparent electrode, 14 is metal electrode, 7 is hole injection layer which is deposited onto 6, 8 is hole transport layer which is deposited onto 7, 9 is electron blocking layer which is deposited onto 8, 10 is delayed fluorescent or phosphorescent emitting layer which is deposited onto 9, 11 is hole blocking layer which is deposited onto 10, 12 is electron transport layer which is deposited onto 11, 13 is electron injection layer which is deposited on to 12.

DESCRIPTION OF THE PREFERRED EMBODIMENTS

What probed into the invention is the material and organic EL device using the material. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the material which can be used as phosphorescent emitting host, delayed fluorescence dopant, and hole blocking layer (HBL) for organic EL device are disclosed. The mentioned the material are represented by the following formula(1) or formula(2)

formula(1)

formula(2)

wherein m represents an integer of 0 to 4, $X_1$ to $X_4$ independently represent a divalent bridge selected from the atom or group consisting from O, S, $C(R_7)(R_8)$, $N(Ar)$, Si($R_9$)($R_{10}$), Ar is selected from the group consisting of a hydrogen, a substituted or unsubstituted aryl group having 6 to 60 carbon atoms or a substituted or unsubstituted heteroaryl group having 3 to 60 carbon atoms, and provided that Ar represents a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted quinoline group, a substituted or unsubstituted isoquinoline group, a substituted or unsubstituted quinazoline group, a substituted or unsubstituted phenanthroline group, a substituted or unsubstituted dihydroacridine group, a substituted or unsubstituted phenothiazine group, a substituted or unsubstituted phenoxazine group, and a substituted or unsubstituted dihydrophenazine group; $R_1$ to $R_{10}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

According to the above-mentioned the material formula (?) or formula(2), wherein the Ar is represented by the following formula(3) to formula(6):

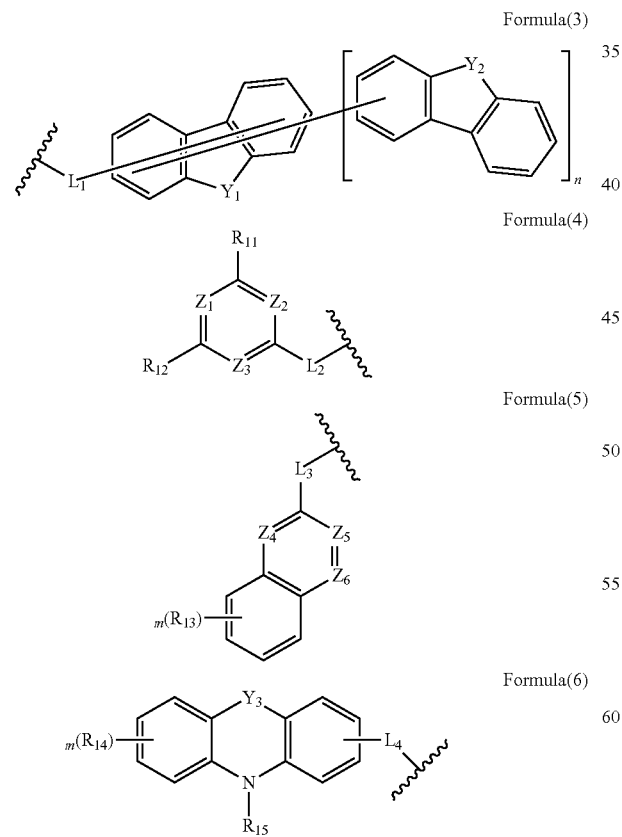

Formula(3)

Formula(4)

Formula(5)

Formula(6)

wherein $L_1$ to $L_4$ represent a single bond, a substituted or unsubstituted arylene group having 6 to 30 ring carbon atoms, or a substituted or unsubstituted heterarylene group having 3 to 30 ring carbon atoms, m represents an integer of 0 to 4, n represents an integer of 0 or 1, $Y_1$ to $Y_3$ independently represent a divalent bridge selected from the atom or group consisting from O, S, C($R_{16}$)($R_{17}$), N($R_{18}$), $Z_1$ to $Z_6$ represent a nitrogen atom or C($R_s$), and each $R_s$ represents a hydrogen, a phenyl, a substituted or unsubstituted alkyl group having 1 to 30 carbon atoms, and a substituted or unsubstituted aryl group having 6 to 30 carbon atoms; $R_{11}$ to $R_{18}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

In this embodiment, some materials are shown below:

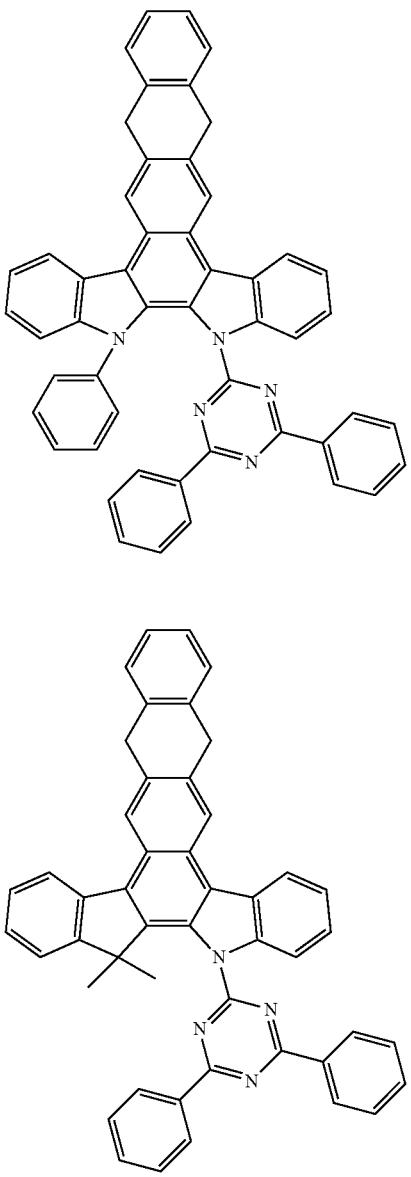

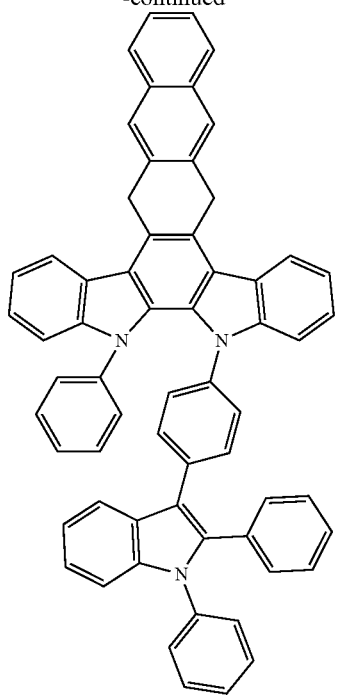
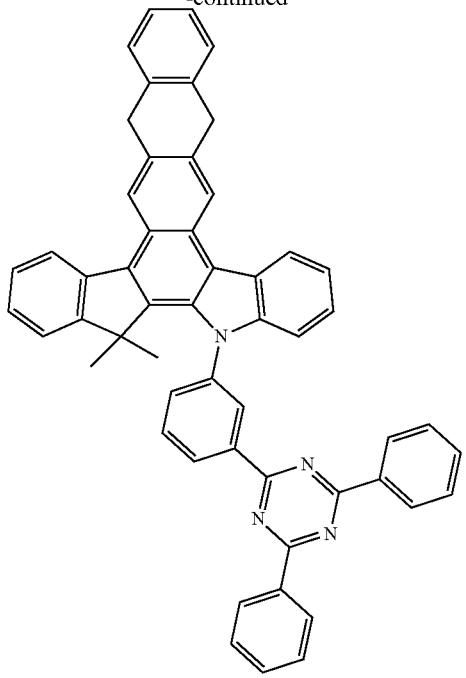
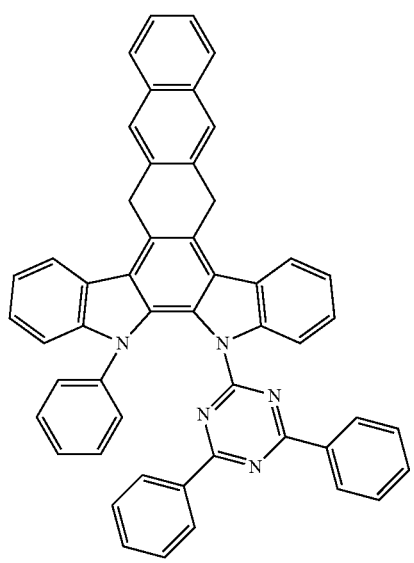
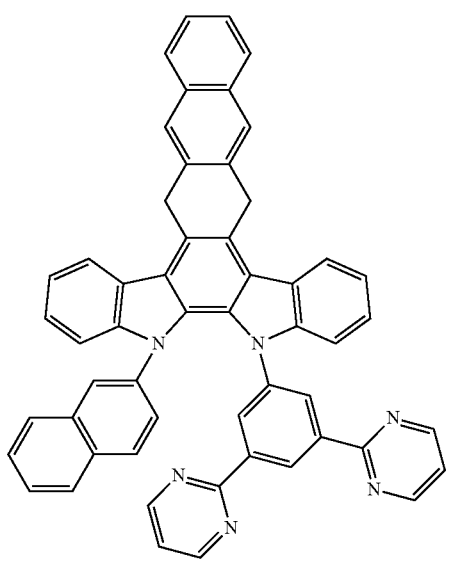

-continued
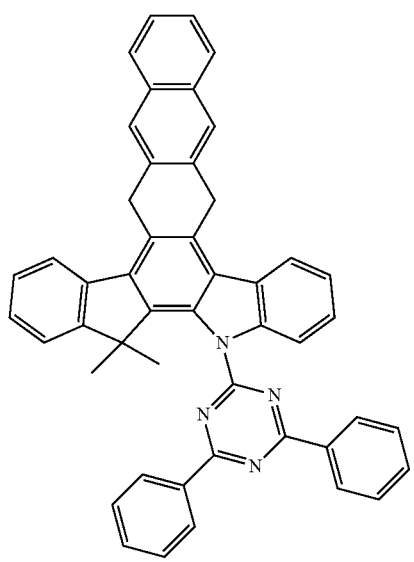
-continued
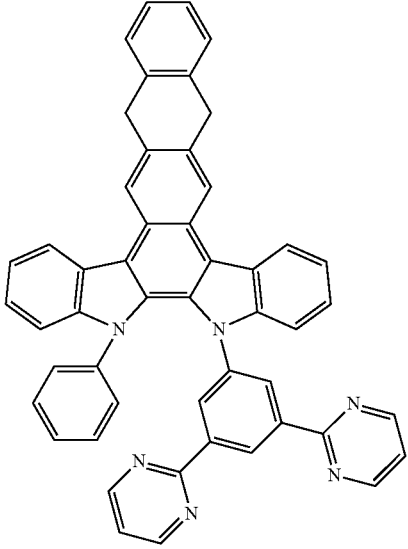

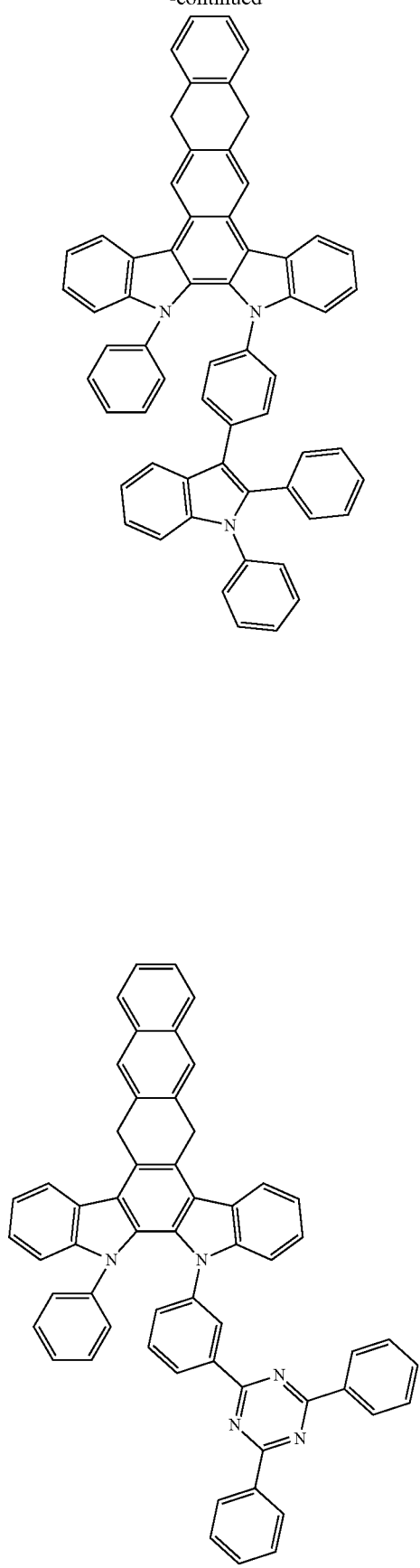
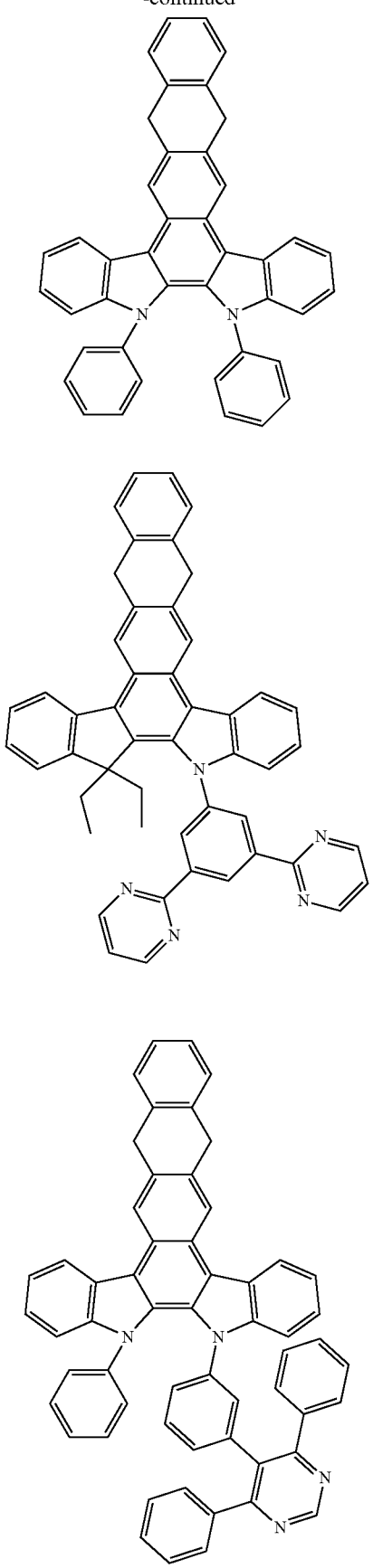

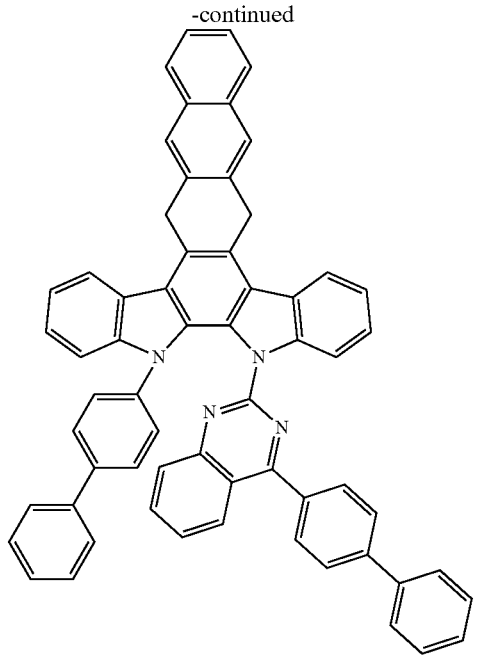
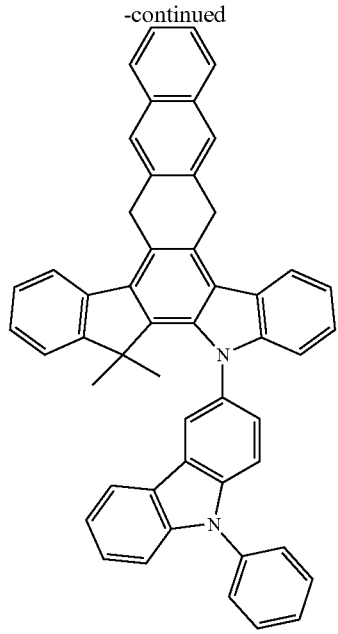
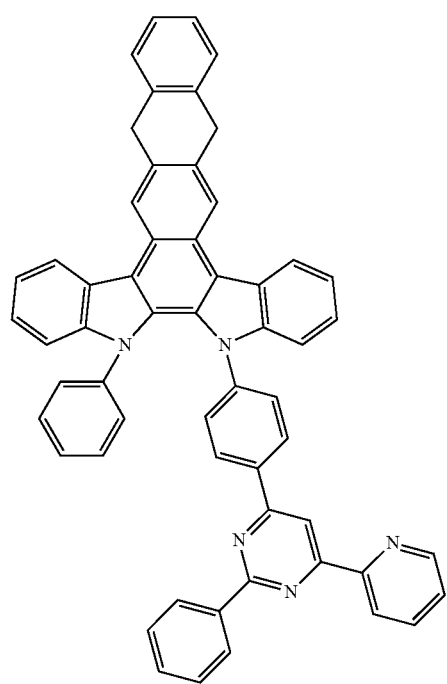
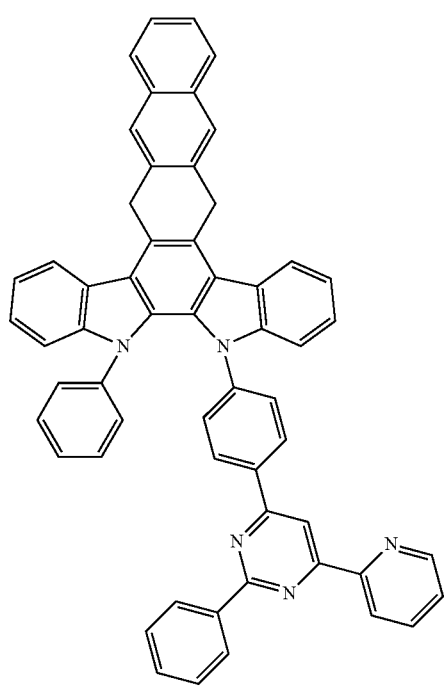

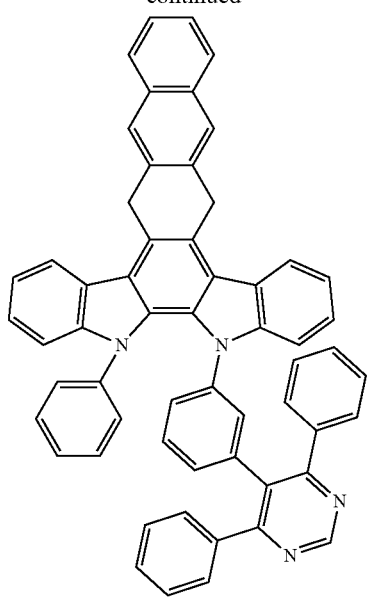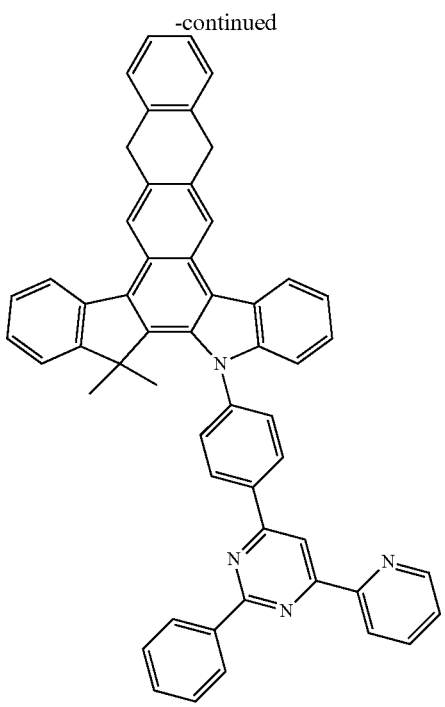

-continued
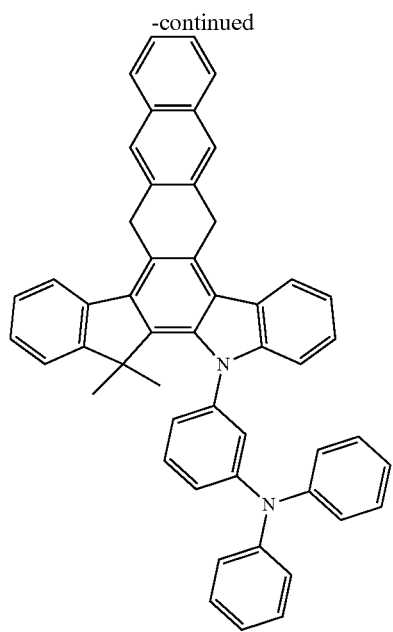
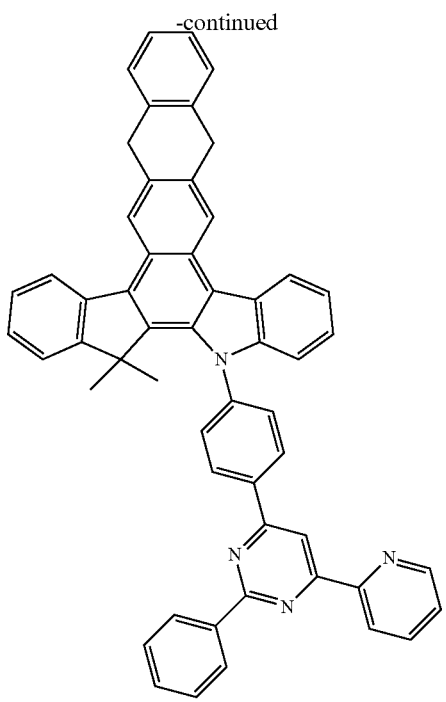
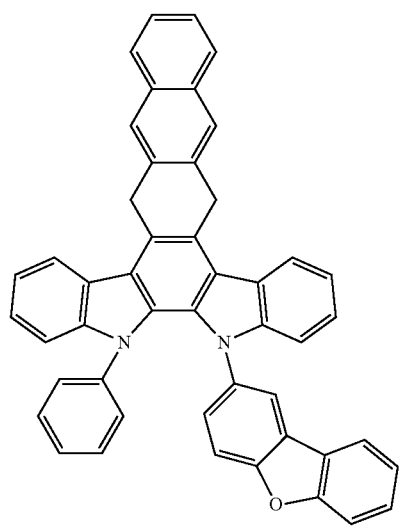
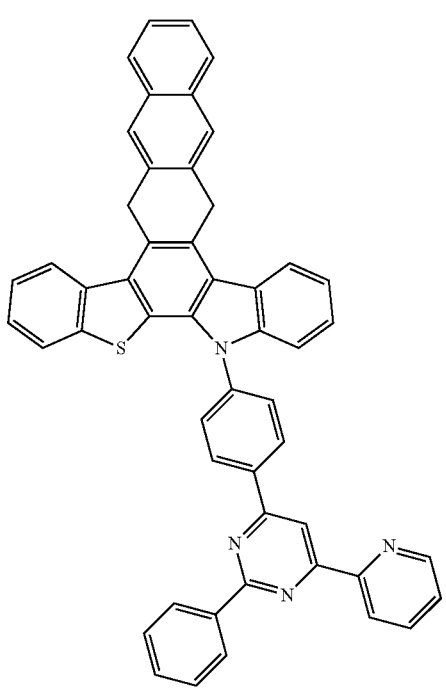

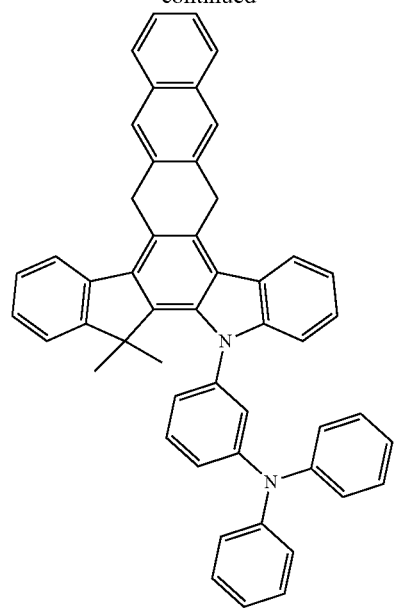
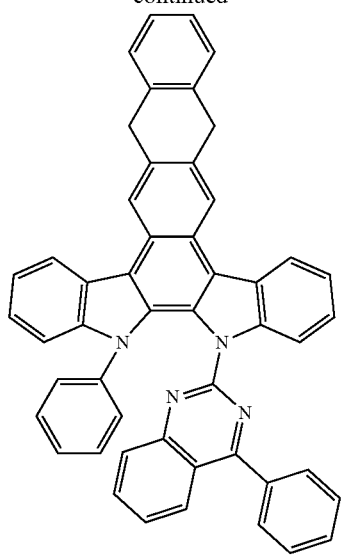
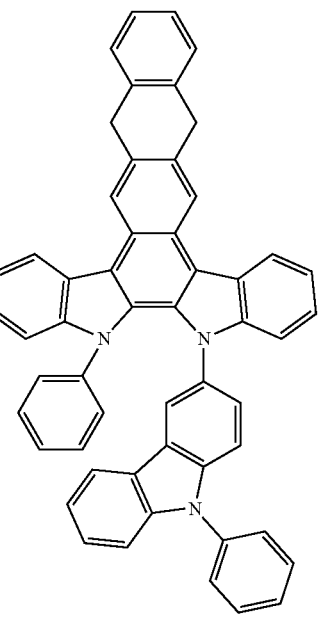
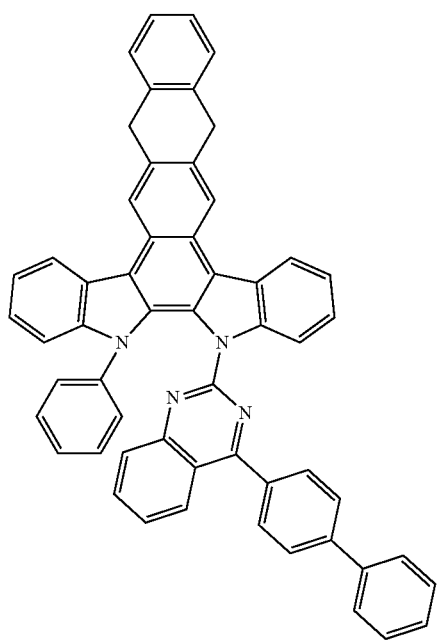
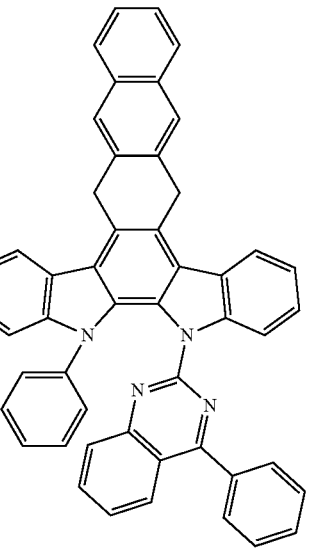

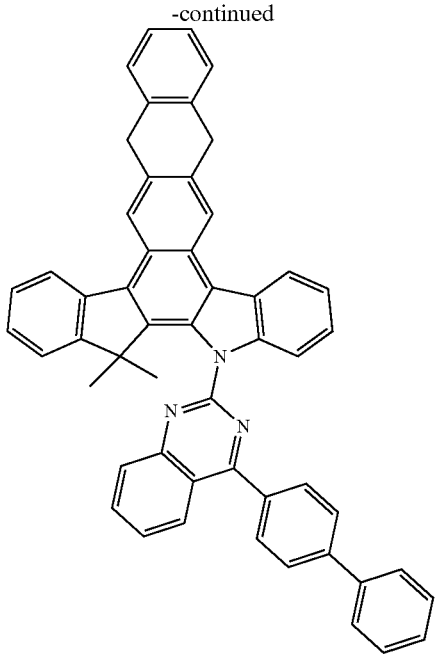
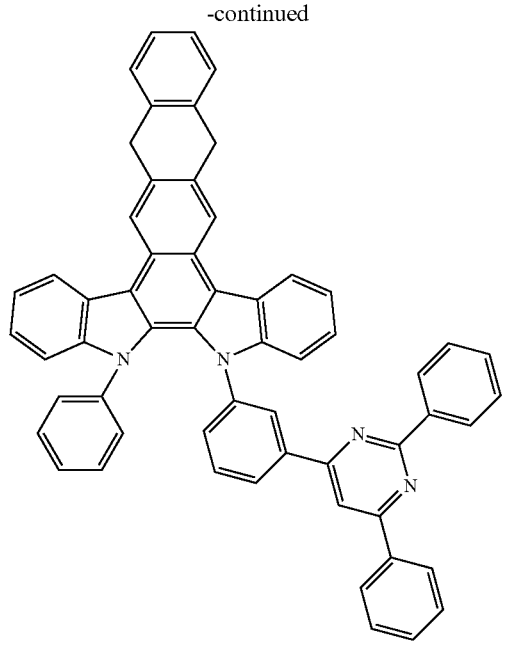
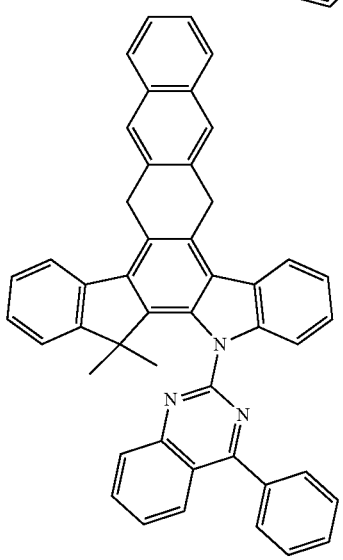
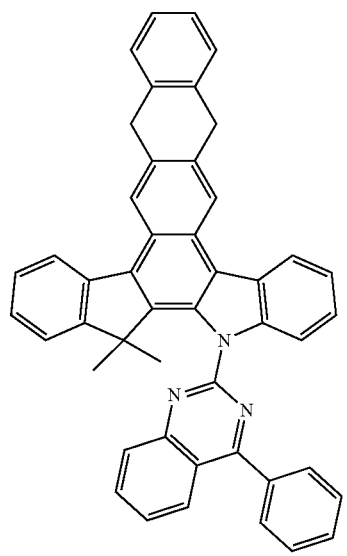
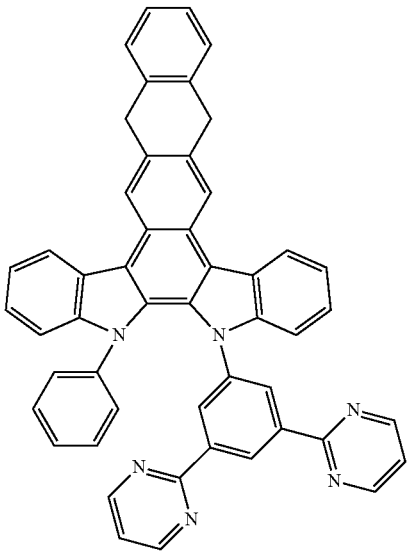

23
-continued
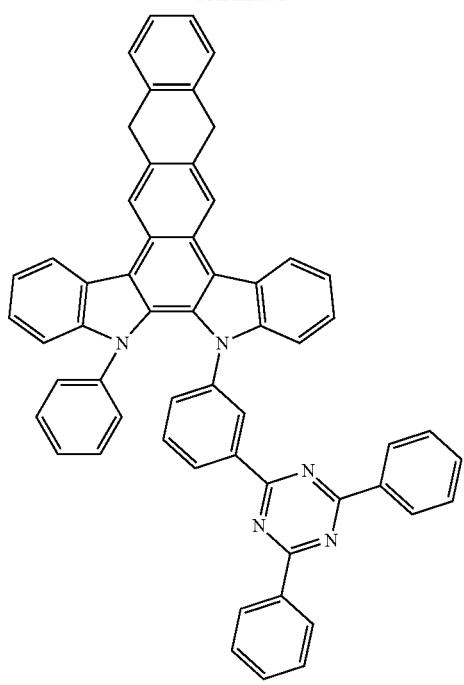
24
-continued
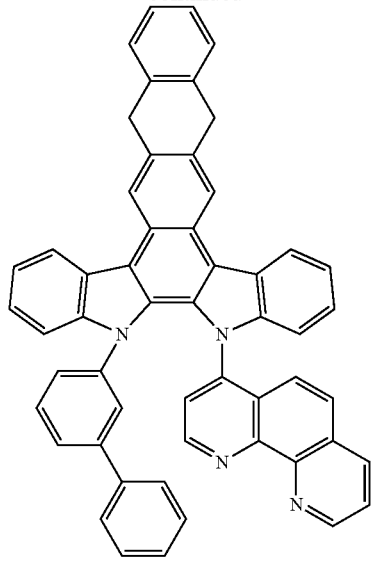
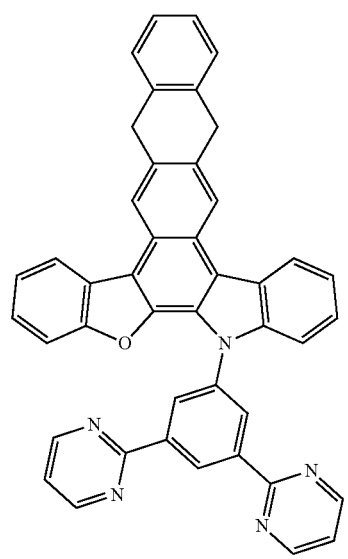
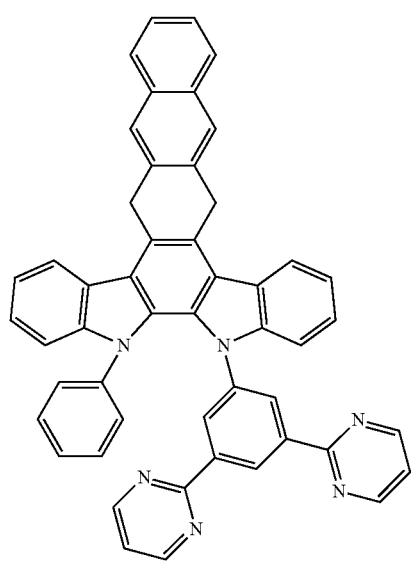
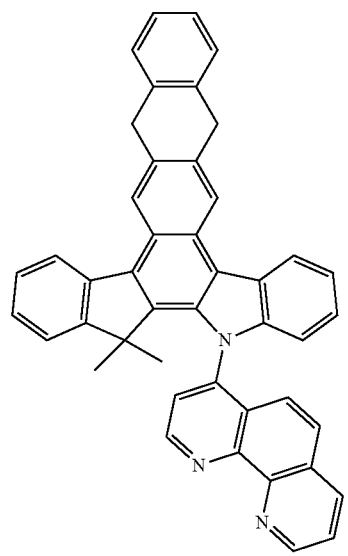

-continued
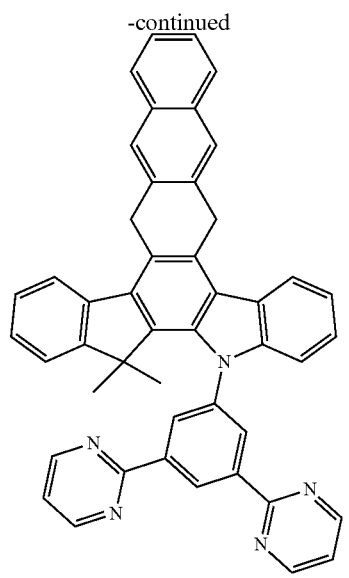
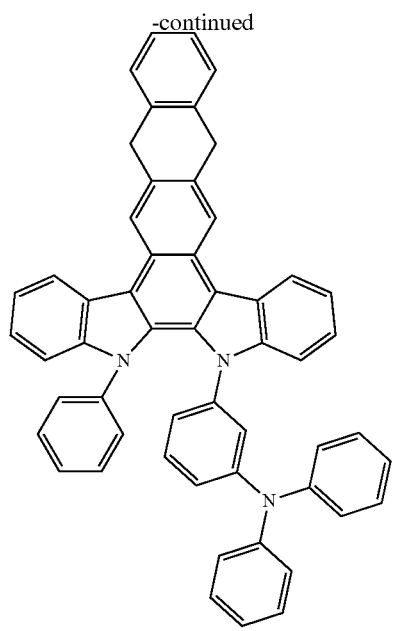
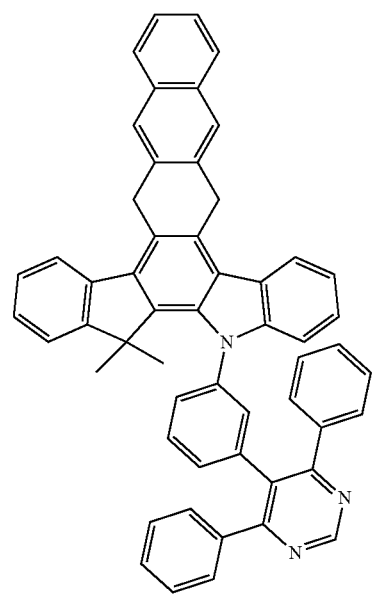
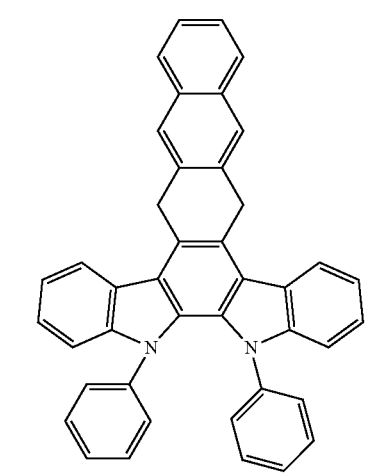
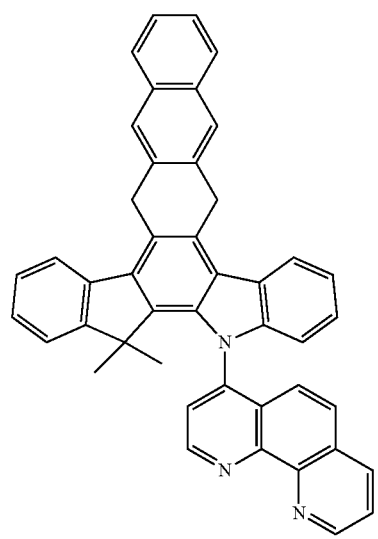
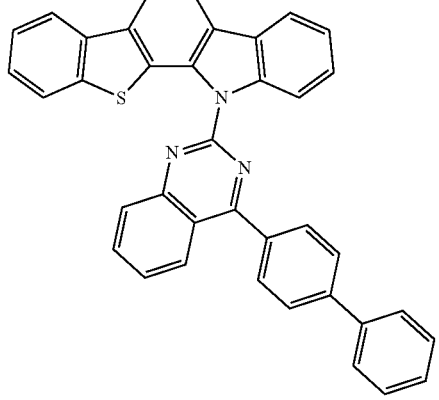

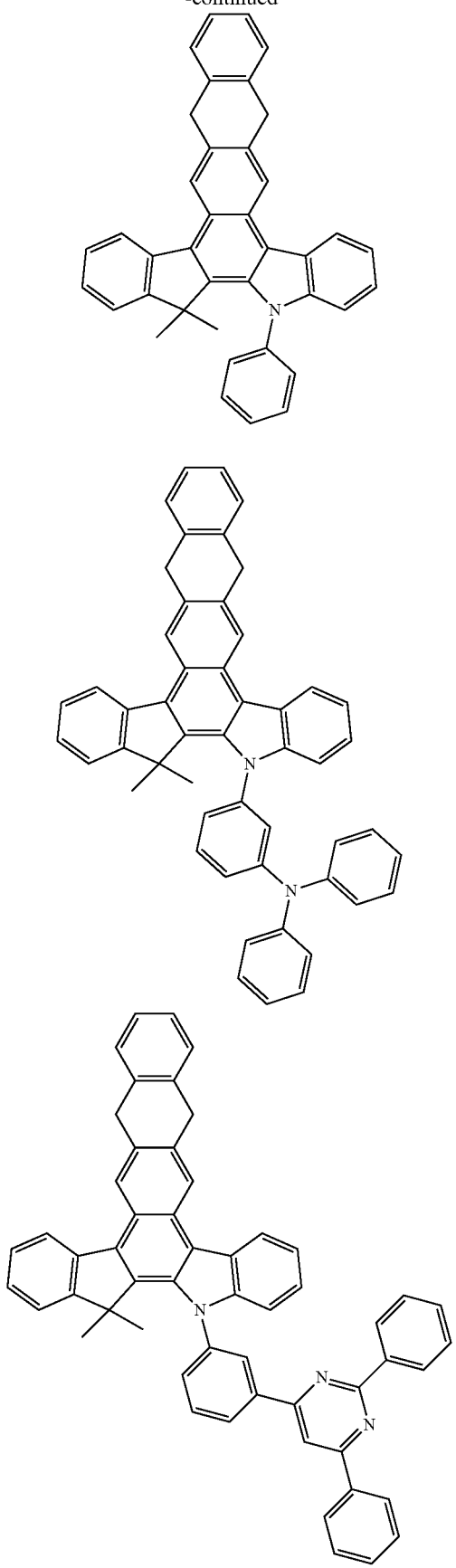

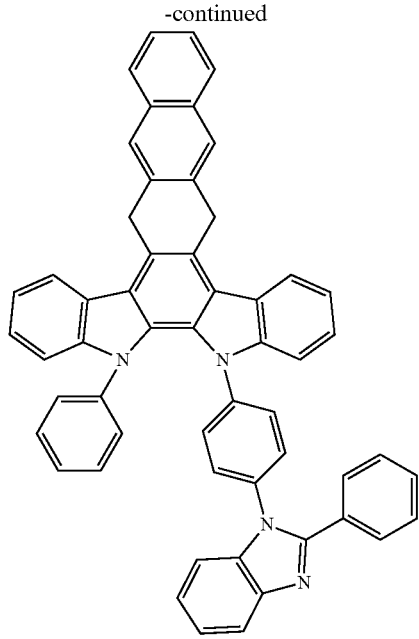
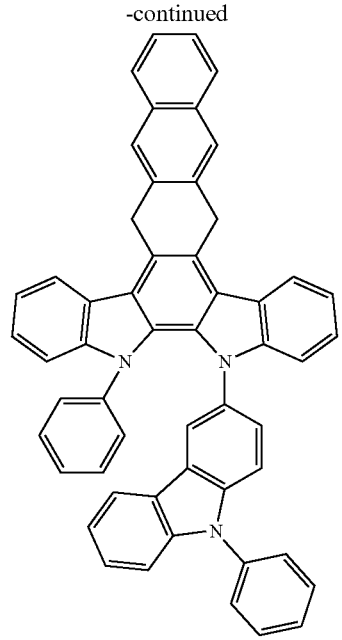
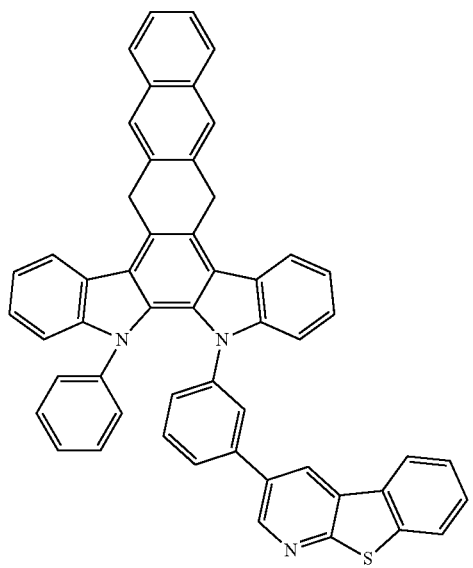
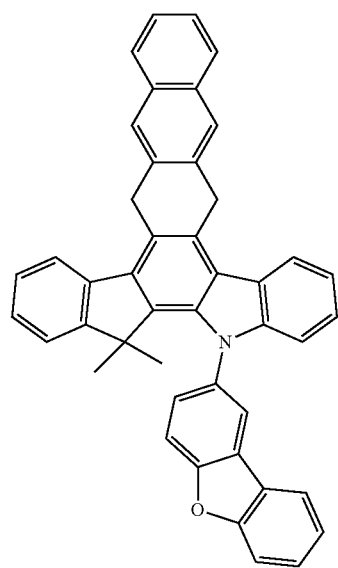

31
-continued
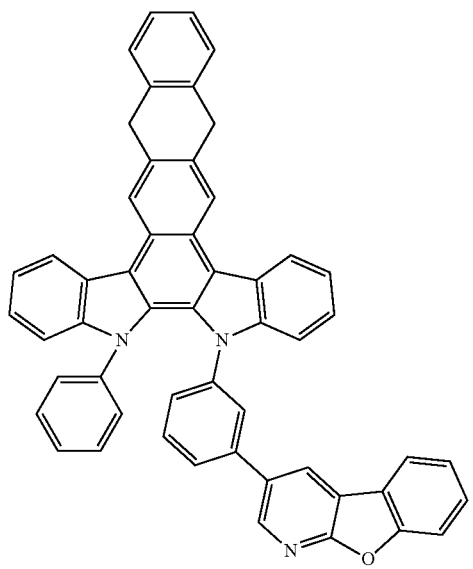
32
-continued
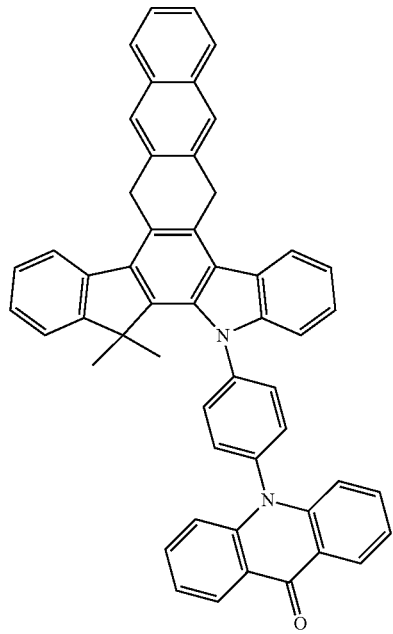
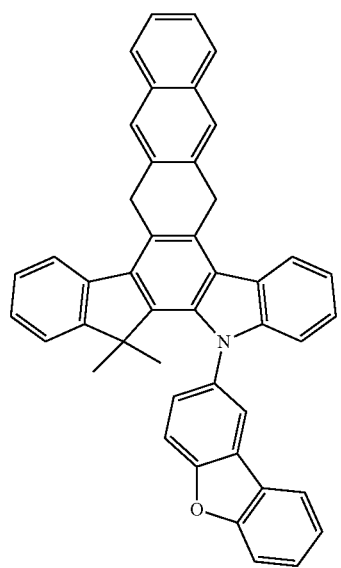
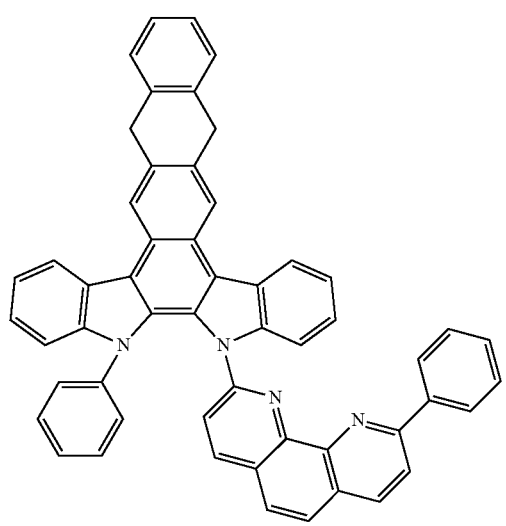

33
-continued
34
-continued
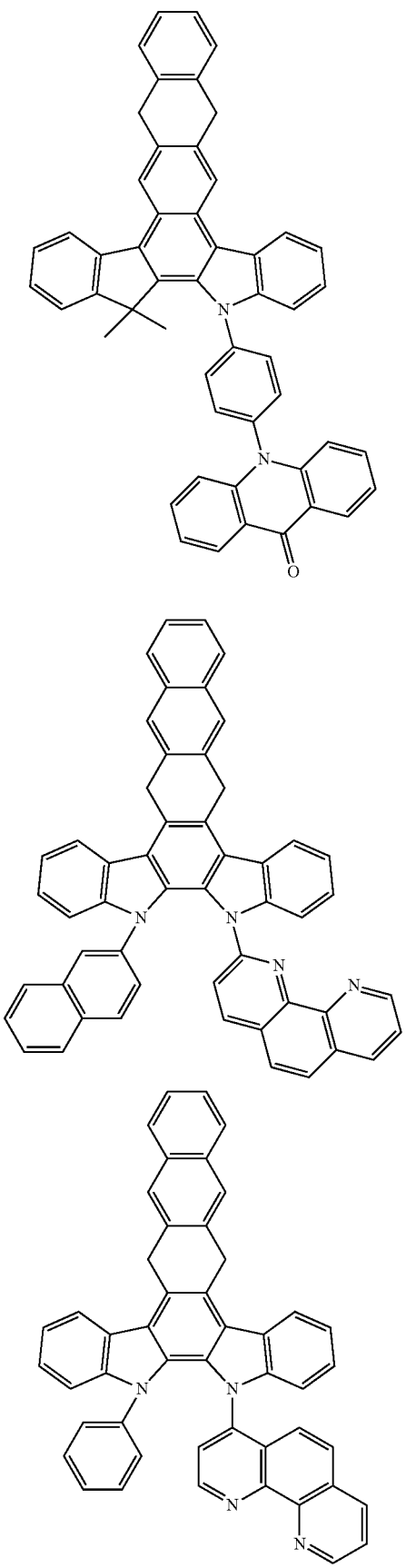
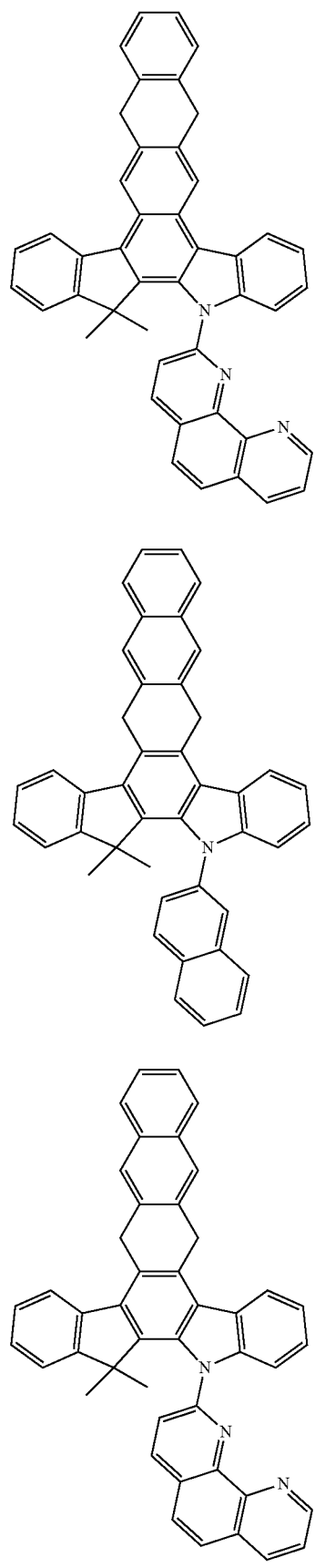

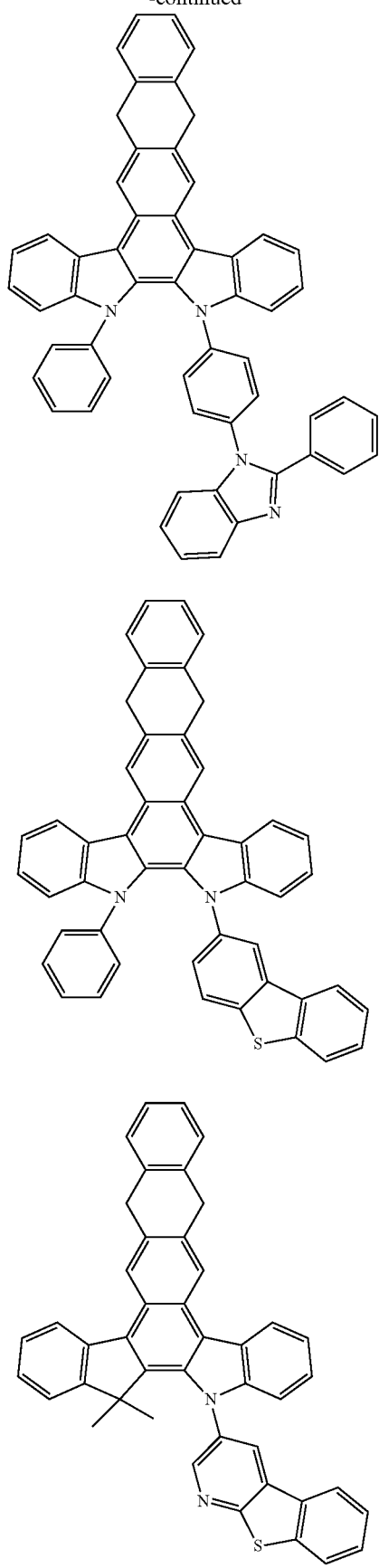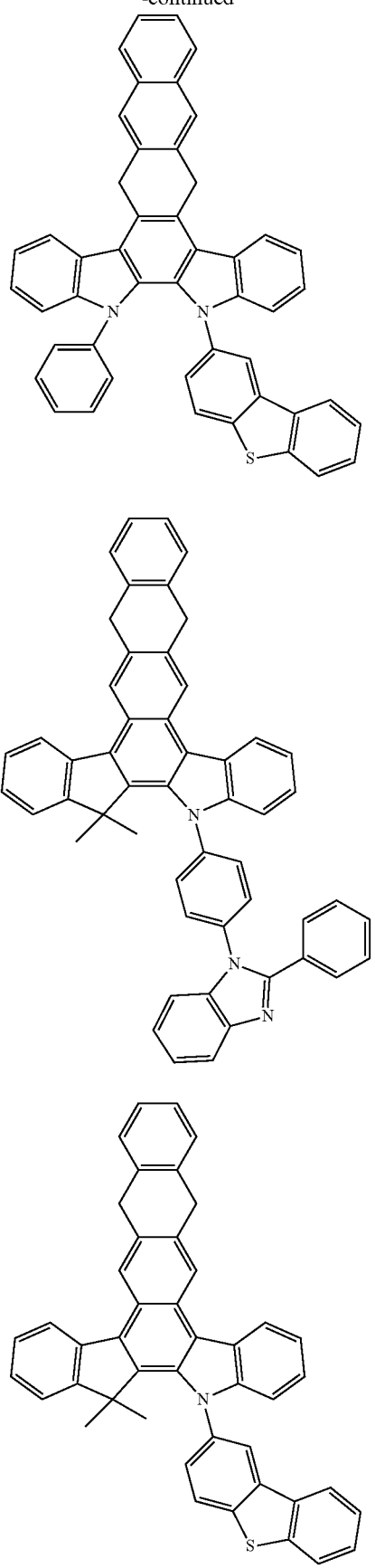

37
-continued
38
-continued
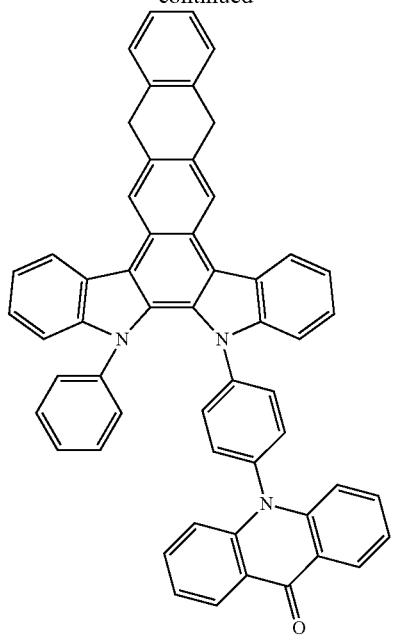
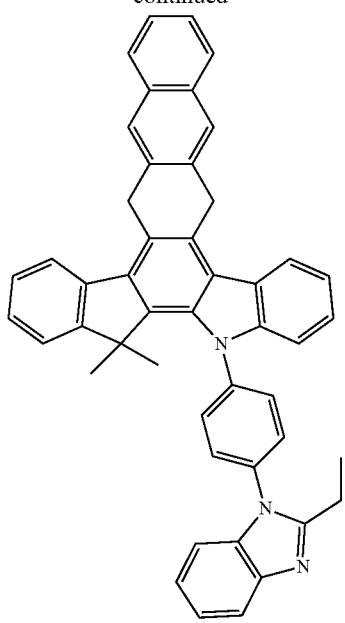

39
-continued
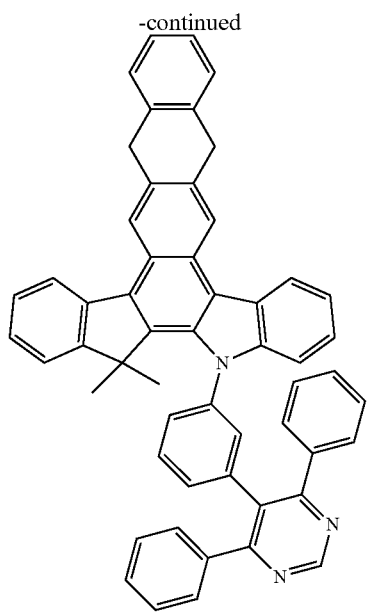
40
-continued
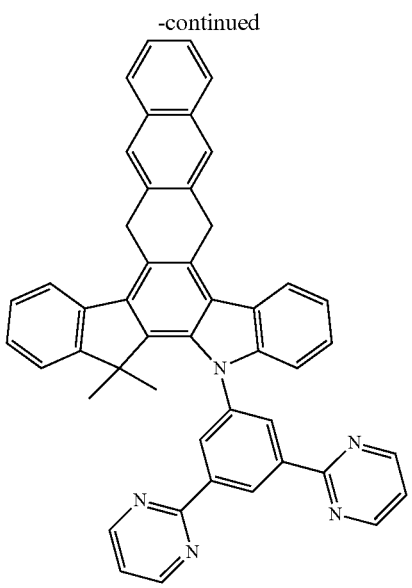
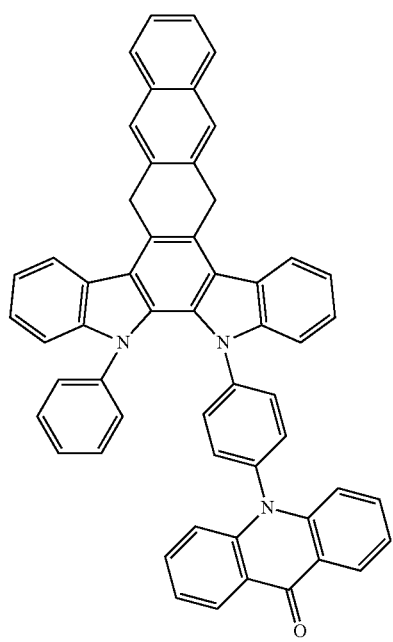
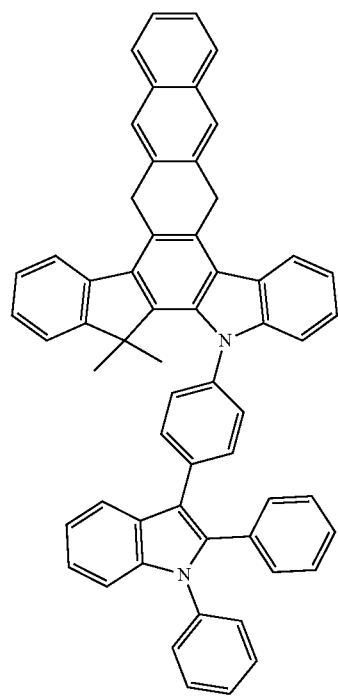

41
-continued
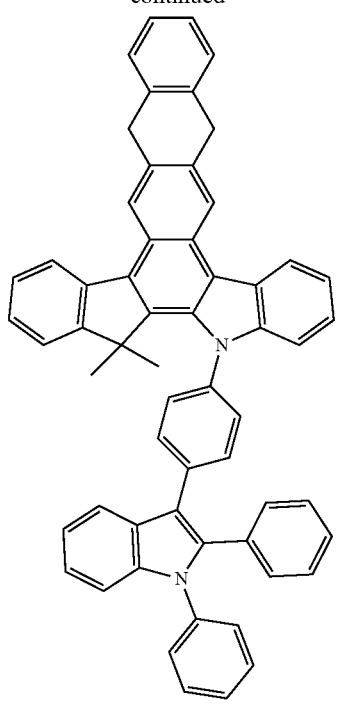
42
-continued
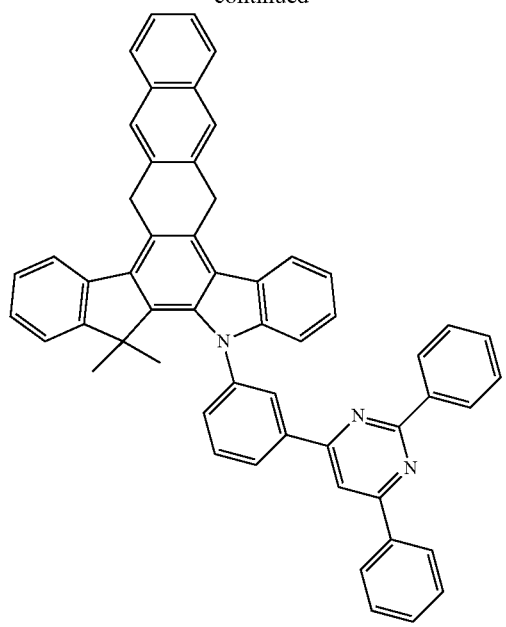
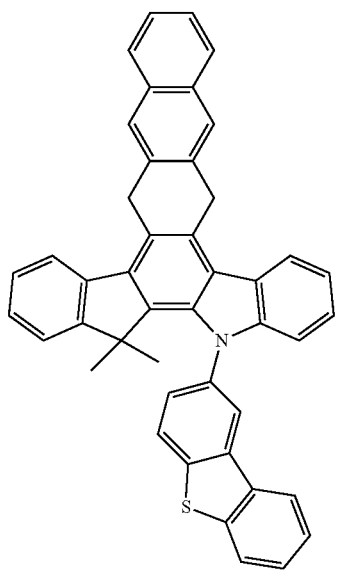
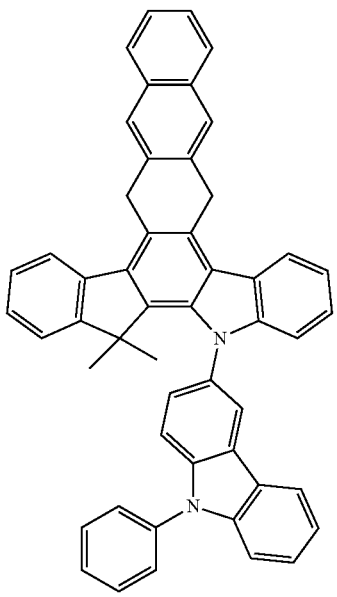

-continued

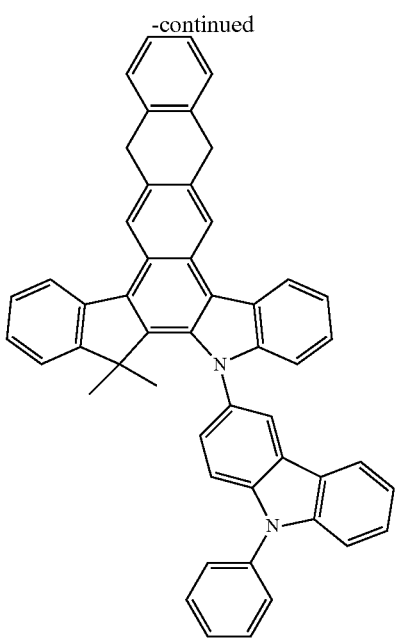

Detailed preparation for the material in the present invention could be clarified by exemplary embodiments, but the present invention is not limited to exemplary embodiments. EXAMPLE 1~4 show the preparation for some EXAMPLES of the material in the present invention. EXAMPLE 6~8 show the fabrication of organic EL device and I-V-B, half-life time of organic EL device testing report.

Example 1

Synthesis of EX1

Synthesis of Intermediate I

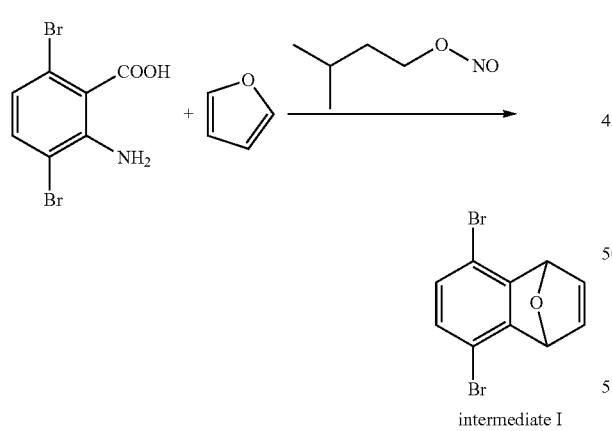

intermediate I

A mixture of 34 g (500 mmol) of furan, 500 ml of 1.2-dimethoxy-ethane, was placed under nitrogen, and then heated to reflux, than 29.3 g (100 mmol) of 2-amino-3,6-dibromobenzoic acid, 11.7 g (100 mmol) of isopentyl nitrite was added to the mixture, and then stirred 1 hour. After finishing the reaction, the mixture was allowed to cool to room temperature. The solution was extracted with 250 ml of ethyl acetate and 1000 ml of water. The organic layer was dried with anhydrous magnesium sulfate and the solvent was evaporated under reduced pressure. The residue was purified by column chromatography on silica gel(hexane-dichloromethane) to give product 9.0 g (33.0 mmol, 33%).

Synthesis of Intermediate II

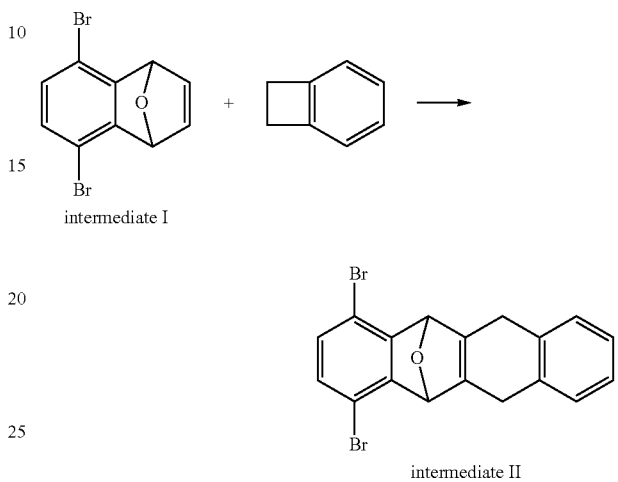

intermediate II

A mixture of 9 g (33 mmol) of intermediate I and 3.4 g (33 mmol) of 1,2-dihydrocyclobutabenzene was placed to the sealed tube and then heated to 220° C. for 6 hours. After finishing the reaction, the residue was purified by column chromatography on silica gel(hexane-dichloromethane) to give product 4.0 g (10.0 mmol, 30%).

Synthesis of 7,10-dibromo-5,12-dihydrotetracene

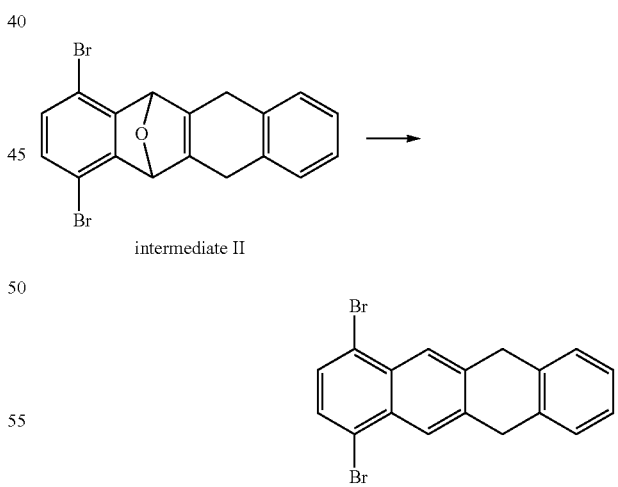

A mixture of 4 g (10 mmol) of intermediate II, 100 ml of acetic anhydride, was placed under nitrogen, 27 ml of HCl was added to the mixture, and then heated to reflux 4 hours. After finishing the reaction, the mixture was allowed to cool to room temperature, 1000 ml of ice water was added, while stirring and the precipitated product was filtered off with suction. To give 2.7 g (7 mmol, yield 70%) of yellow product which was recrystallized from MeOH.

Synthesis of 7,10-bis(2-nitrophenyl)-5,12-dihydrotetracene

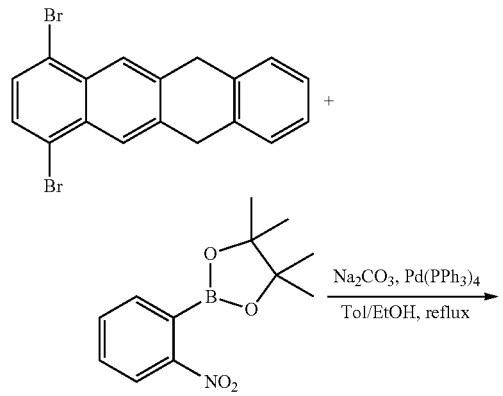

A mixture of 3.9 g (10 mmol) of 7,10-dibromo-5,12-dihydrotetracene, 5.2 g (22 mmol) of 4,4,5,5-tetramethyl-2-(2-nitrophenyl)-1,3,2-dioxaborolane, 0.231 g (0.2 mmol) of Pd(PPh$_3$)$_4$, 20 ml of 2M Na$_2$CO$_3$, 30 ml of EtOH and 80 ml toluene was degassed and placed under nitrogen, and then heated at 100° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica gel to give product 3.2 g (6.8 mmol, 68%) as a yellow solid.

Synthesis of 5,6,12,17-tetrahydroanthra[2,3-c]indolo [2,3-a]carbazole

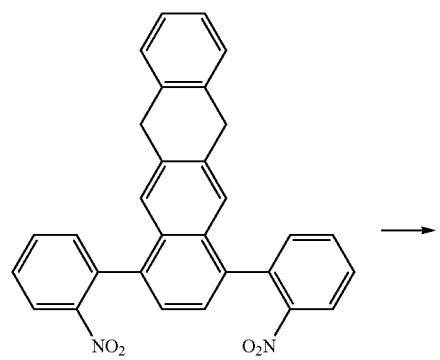

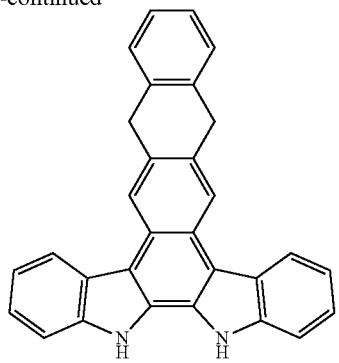

A mixture of 3.2 g (6.8 mmol) of 7,10-bis(2-nitrophenyl)-5,12-dihydrotetracene, 20 ml of triethylphosphite, 10 ml of 1,2-dichlorobenzene, was placed under nitrogen, and then heated at 160° C. overnight. After finishing the reaction, the mixture was allowed to cool to room temperature. Than 100 ml of MeOH was added, while stirring and the precipitated product was filtered off with suction. To give 2.4 g (5.8 mmol, yield 85%) of yellow product which was recrystallized from toluene.

Synthesis of 5-phenyl-5,6,12,17-tetrahydroanthra[2,3-c]indolo [2,3-a]carbazole

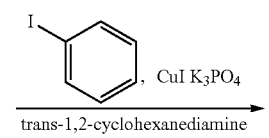

A mixture of 2.4 g (5.6 mmole) 5,6,12,17-tetrahydroanthra[2,3-c] indolo[2,3-a]carbazole, 1.4 g (7 mmol) of iodobenzene, 11.4 g (60 mmole) of copper(I) iodide, 12.6 g (60 mmole) of potassium phosphate, 3.8 g (60 mmole) of trans-1,2-cyclohexanediamine and 1,4-dioxane 100 ml were refluxed under nitrogen for about overnight. Then, the solution was filtered at 110° C. To receive the filtrate. And the 1,4-dioxane was removed under reduced pressure from the filtrate. To give 1.4 g (2.9 mmol, yield 51%) of yellow product which was recrystallized from toluene.

Synthesis of EX1

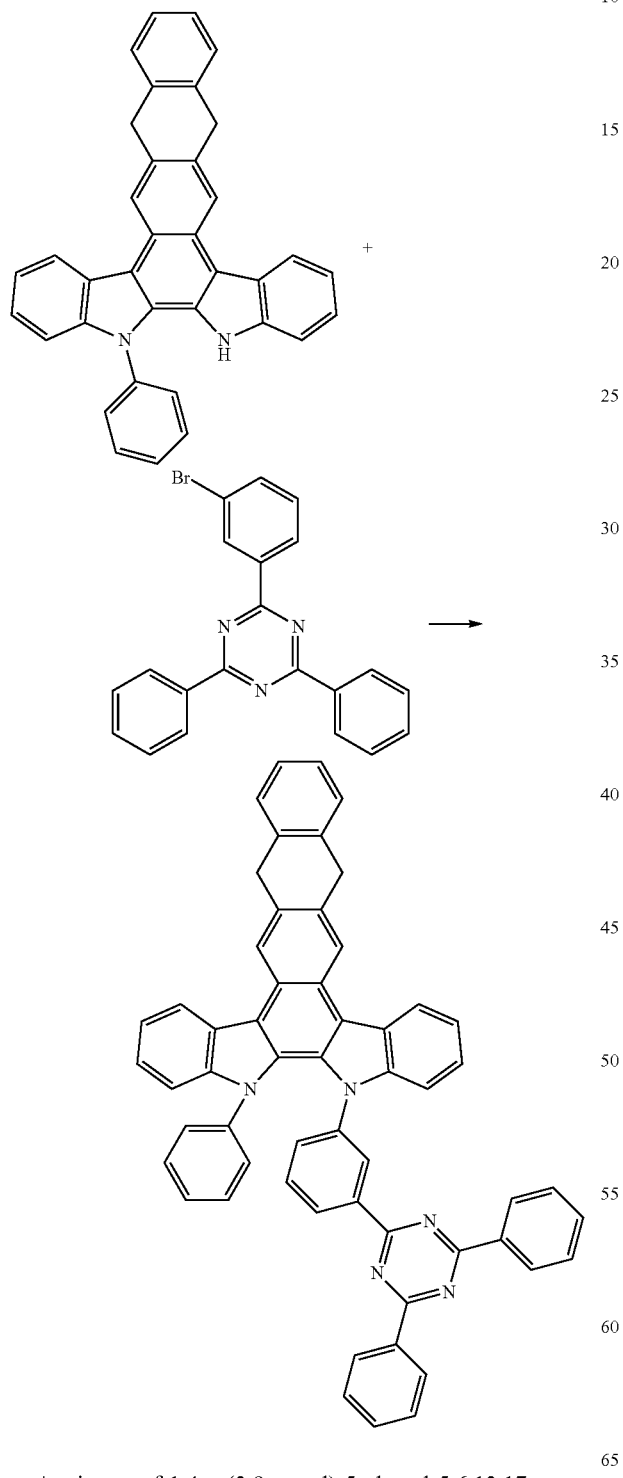

A mixture of 1.4 g (2.9 mmol) 5-phenyl-5,6,12,17-tetrahydroanthra [2,3-c]indolo[2,3-a]carbazole, 1.9 g (5 mmol) of 2-(3-bromophenyl)-4,6-diphenyl-1,3,5-triazine, 0.05 g (0.2 mmol) of palladium(II)acetate, 0.15 g (0.4 mmol) of 2-(dicyclohexylphosphino)biphenyl, 1 g (10 mmol) of sodium tert-butoxide and 50 ml of toluene was refluxed under nitrogen overnight. After finishing the reaction, the yellow precipitate formed was vacuum filtered and washed with ethanol and hexanes. To give 1.5 g (yield 64%) of yellow product which was recrystallized from toluene and purified by vacuum sublimation. MS (m/z, FAB$^+$): 793.3; 1H NMR(CDCl$_3$, 500 MHz): chemical shift (ppm) 8.60~8.56 (m, 2H), 8.45~8.25 (m, 3H), 8.29~8.21 (m, 3H), 8.15~8.07 (m, 4H), 7.86~7.54 (m, 5H), 7.48~7.33 (m, 10H), 7.05~7.01 (m, 5H), 6.85~6.81 (m, 1H), 4.03~3.98 (m, 4H).

Example 2

Synthesis of EX2

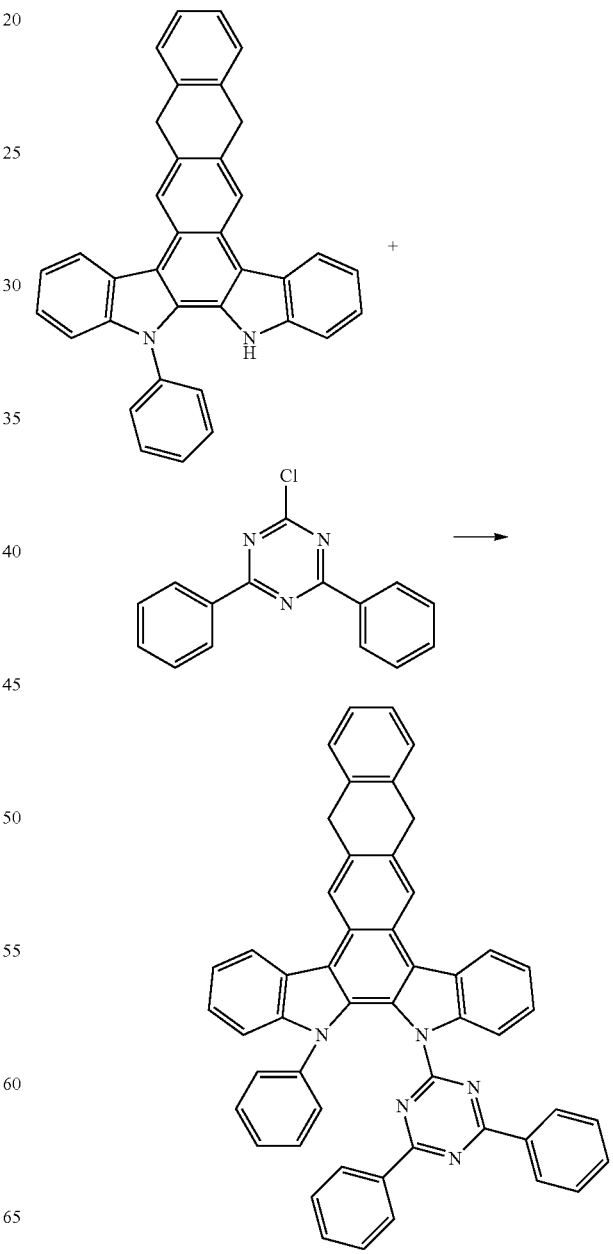

Under N₂ condition, 16.5 g (23 mmol) 5-phenyl-5,6,12,17-tetrahydroanthra[2,3-c]indolo[2,3-a]carbazole and 200 ml of DMF were mixed, and 4.4 g (184 mmol) of NaH was slowly added to the mixture. The mixture was stirred at room temperature for 30 minutes. Than 21.4 g (55.2 mmol) of 2-chloro-4,6-diphenyl-1,3,5-triazine was slowly added to the mixture. The mixture was stirred at room temperature for 24 hours. After completion of the reaction, 1000 ml of iced water was added, while stirring and the precipitated product was filtered off with suction. To give 6.0 g (yield 31%) of yellow product which was recrystallized from ethyl acetate and purified by vacuum sublimation. MS (m/z, FAB⁺): 715.2; 1H NMR (CDCl₃, 500 MHz): chemical shift (ppm) 8.59~8.54 (m, 2H), 8.43~8.31 (m, 2H), 8.25~8.21 (m, 2H), 8.14~8.03 (m, 3H), 7.86~7.54 (m, 5H), 7.47~7.30 (m, 9H), 7.05~7.01 (m, 5H), 6.85~6.81 (m, 1H), 4.05~3.98 (m, 4H).

Example 3

Synthesis of Intermediate III

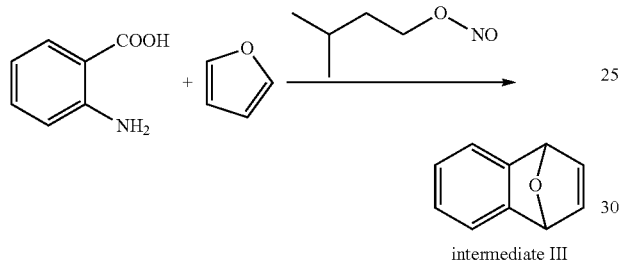

intermediate III

A mixture of 34 g (500 mmol) of furan, 500 ml of 1.2-dimethoxyethane, was placed under nitrogen, and then heated to reflux, than 13.7 g (100 mmol) of 2-aminobenzoic acid, 11.7 g (100 mmol) of isopentyl nitrite was added to the mixture, and then stirred 1 hour. After finishing the reaction, the mixture was allowed to cool to room temperature the solution was extracted with 250 ml of ethyl acetate and 1000 ml of water. The organic layer was dried with anhydrous magnesium sulfate and the solvent was evaporated under reduced pressure. The residue was purified by column chromatography on silica gel(hexane-dichloromethane) to give product 5.9 g (41.0 mmol, 41%).

Synthesis of Intermediate IV

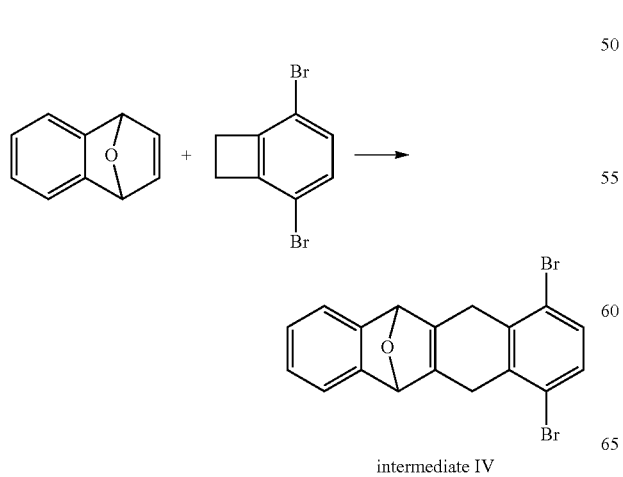

intermediate IV

A mixture of 5.9 g (41 mmol) of intermediate III and 11.4 g (44 mmol) of 3,6-dibromo-1,2-dihydrocyclobutabenzene was placed to the sealed tube and then heated to 220° C. for 6 hours. After finishing the reaction, the residue was purified by column chromatography on silica gel(hexane-dichloromethane) to give product 7.1 g (17.6 mmol, 43%).

Synthesis of 1,4-dibromo-5,12-dihydrotetracene

A mixture of 4 g (10 mmol) of intermediate IV, 100 ml of acetic anhydride, was placed under nitrogen, 27 ml of HCl was added to the mixture, and then heated to reflux 4 hours. After finishing the reaction, the mixture was allowed to cool to room temperature, 1000 ml of ice water was added, while stirring and the precipitated product was filtered off with suction. To give 3.1 g (8.1 mmol, yield 81%) of yellow product which was recrystallized from MeOH.

Synthesis of 1,4-bis(2-nitrophenyl)-5,12-dihydrotetracene

-continued

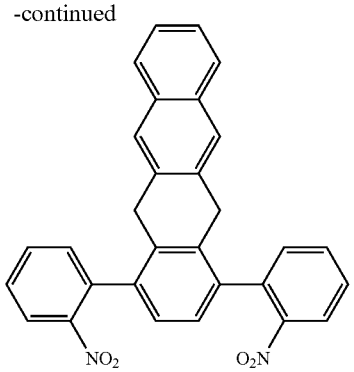

A mixture of 3.8 g (10 mmol) of 1,4-dibromo-5,12-dihydrotetracene, 5.2 g (22 mmol) of 4,4,5,5-tetramethyl-2-(2-nitrophenyl)-1,3,2-dioxaborolane, 0.231 g (0.2 mmol) of Pd(PPh$_3$)$_4$, 20 ml of 2M Na$_2$CO$_3$, 30 ml of EtOH and 80 ml toluene was degassed and placed under nitrogen, and then heated at 100° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica gel to give product 3.6 g (7.6 mmol, 76%) as a yellow solid.

Synthesis of 5,6,11,18-tetrahydroanthra[2,3-c]indolo[2,3-a]carbazole

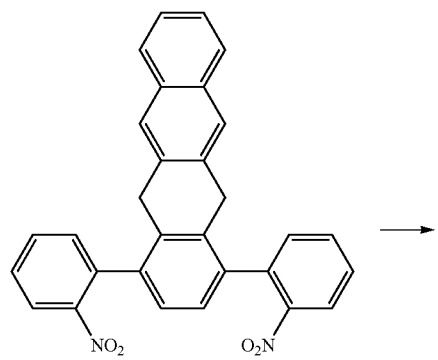

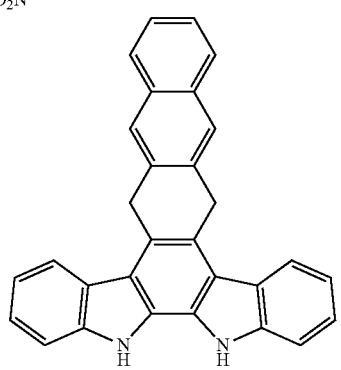

A mixture of 3.6 g (7.6 mmol) of 1,4-bis(2-nitrophenyl)-5,12-dihydrotetracene, 20 ml of triethylphosphite, 10 ml of 1,2-dichlorobenzene, was placed under nitrogen, and then heated at 160° C. overnight. After finishing the reaction, the mixture was allowed to cool to room temperature. Than 100 ml of MeOH was added, while stirring and the precipitated product was filtered off with suction. To give 2.5 g (6 mmol, yield 80%) of yellow product which was recrystallized from toluene.

Synthesis of 5-phenyl-5,6,11,18-tetrahydroanthra[2,3-c]indolo [2,3-a]carbazole

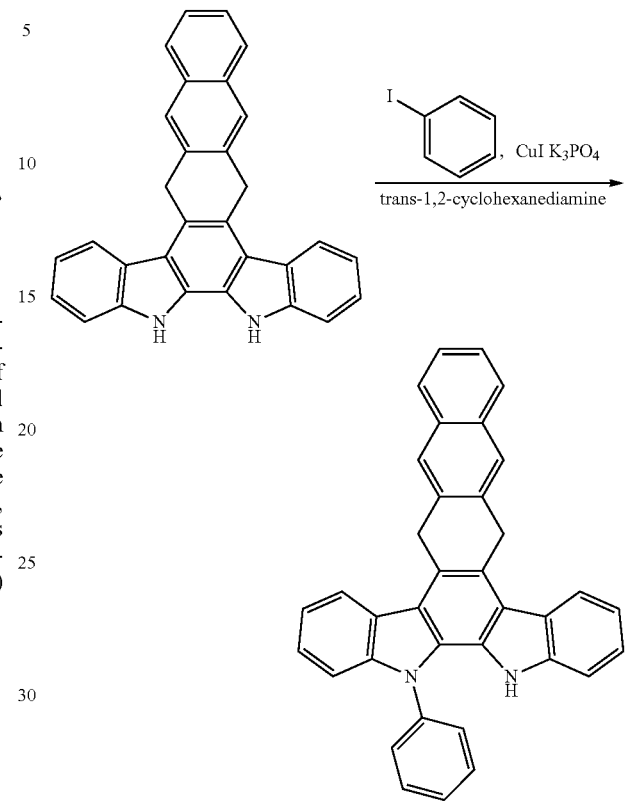

A mixture of 2.5 g (6.0 mmole) 5,6,11,18-tetrahydroanthra[2,3-c]indolo[2,3-a]carbazole, 1.4 g (7 mmol) of iodobenzene, 11.4 g (60 mmole) of copper(I) iodide, 12.6 g (60 mmole) of potassium phosphate, 3.8 g (60 mmole) of trans-1,2-cyclohexanediamine and 1,4-dioxane 100 ml were refluxed under nitrogen for about overnight. Then, the solution was filtered at 110° C. To receive the filtrate. And the 1,4-dioxane was removed under reduced pressure from the filtrate. To give 1.7 g (3.5 mmol, yield 59%) of yellow product which was recrystallized from toluene.

Synthesis of EX3

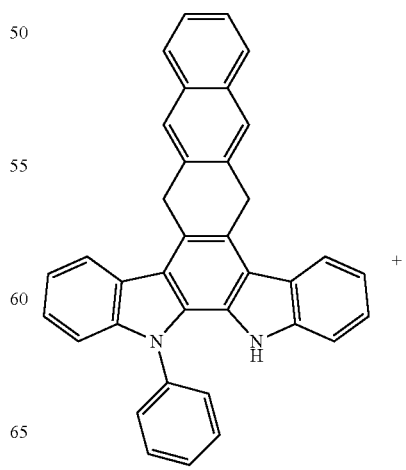
+

53
-continued

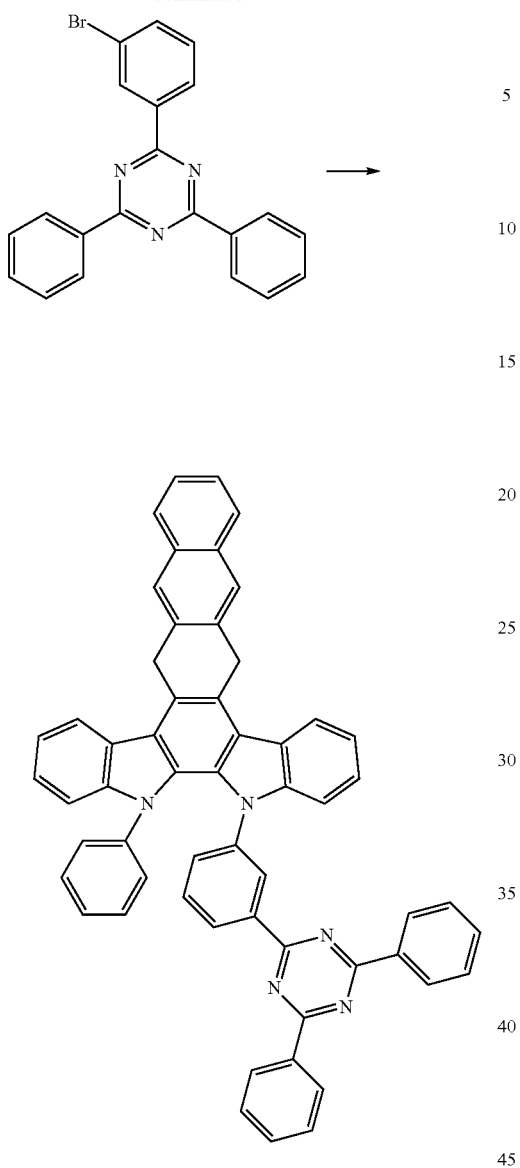

A mixture of 1.4 g (2.9 mmol) 5-phenyl-5,6,11,18-tetrahydroanthra [2,3-c]indolo[2,3-a]carbazole, 1.9 g (5 mmol) of 2-(3-bromophenyl)-4,6-diphenyl-1,3,5-triazine, 0.05 g (0.2 mmol) of palladium(II)acetate, 0.15 g (0.4 mmol) of 2-(dicyclohexylphosphino)biphenyl, 1 g (10 mmol) of sodium tert butoxide and 50 ml of toluene was refluxed under nitrogen overnight. After finishing the reaction, the yellow precipitate formed was vacuum filtered and washed with ethanol and hexanes. To give 1.7 g (yield 72%) of yellow product which was recrystallized from toluene and purified by vacuum sublimation. MS (m/z, FAB+):791.1; 1H NMR (CDCl$_3$, 500 MHz): chemical shift (ppm) 8.60~8.56 (m, 2H), 8.4~8.25 (m, 3H), 8.29~8.21 (m, 3H), 8.15~8.07 (m, 4H), 7.86~7.54 (m, 5H), 7.48~7.33 (m, 10H), 7.05~7.01 (m, 5H), 6.86~6.81 (m, 1H), 4.02~3.99 (m, 4H).

54

Example 4

Synthesis of EX4

Synthesis of Example 4

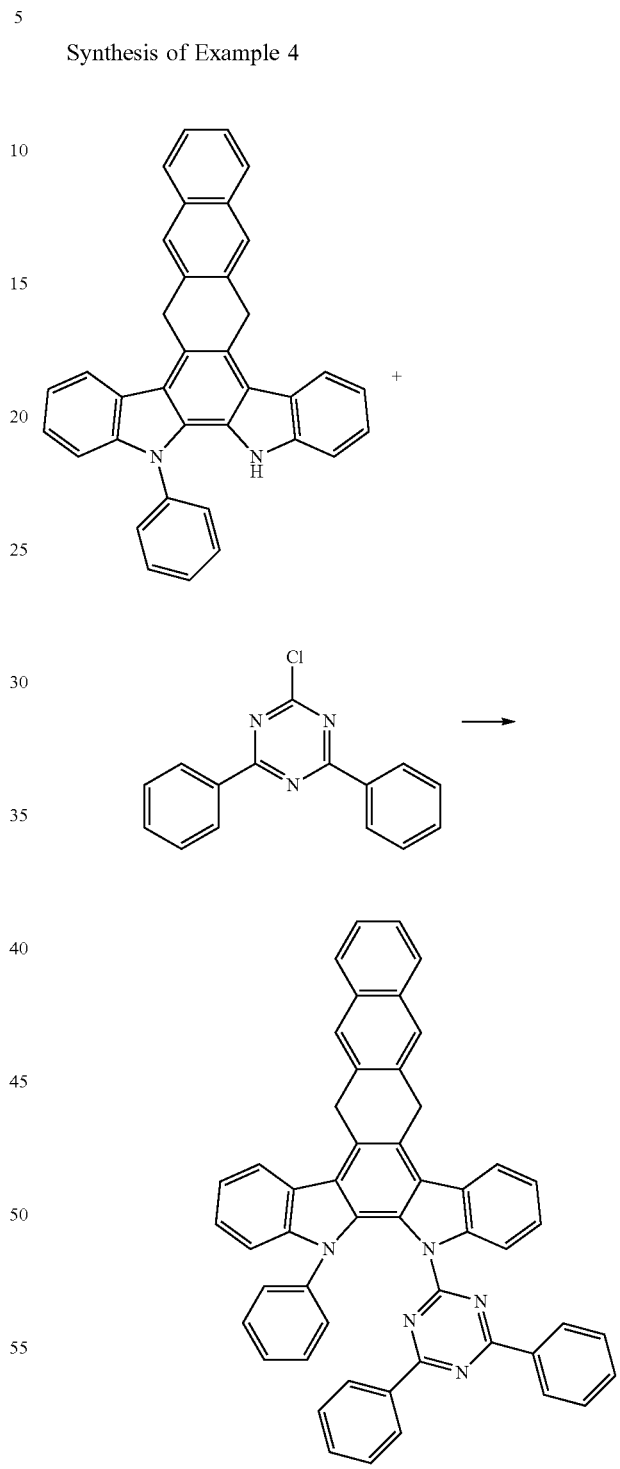

Under N$_2$ condition, 11.1 g (23 mmol) 5-phenyl-5,6,11,18-tetrahydroanthra[2,3-c]indolo[2,3-a]carbazole and 200 ml of DMF were mixed, and 4.4 g (184 mmol) of NaH was slowly added to the mixture. The mixture was stirred at room temperature for 30 minutes. Than 21.4 g (55.2 mmol) of 2-chloro-4,6-diphenyl-1,3,5-triazine was slowly added to the mixture. The mixture was stirred at room temperature for 24 hours. After completion of the reaction, 1000 ml of iced water was added, while stirring and the precipitated product was filtered off with suction. To give 7.7 g (yield 47%) of yellow product which was recrystallized from ethyl acetate and purified by vacuum sublimation. MS (m/z, FAB+): 715.3; 1H NMR(CDCl$_3$, 500 MHz): chemical shift (ppm) 8.57~8.54 (m, 2H), 8.41~8.29 (m, 2H), 8.24~8.20 (m, 2H), 8.11~8.06 (m, 3H), 7.84~7.64 (m, 5H), 7.44~7.32 (m, 9H), 7.04~7.01 (m, 5H), 6.85~6.81 (m, 1H), 3.99~3.95 (m, 4H).

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device, and N,N-Bis (naphthalene-1-yl)-N,N-bis (phenyl)-benzidine (NPB) is most widely used as the hole transporting layer, N-(biphenyl-4-yl)-9,9-dimethyl-N-(4'-phenylbiphenyl-4-yl)-9H-fluoren-2-amine (EB2) is used as electron blocking layer, and the chemical structure shown below:

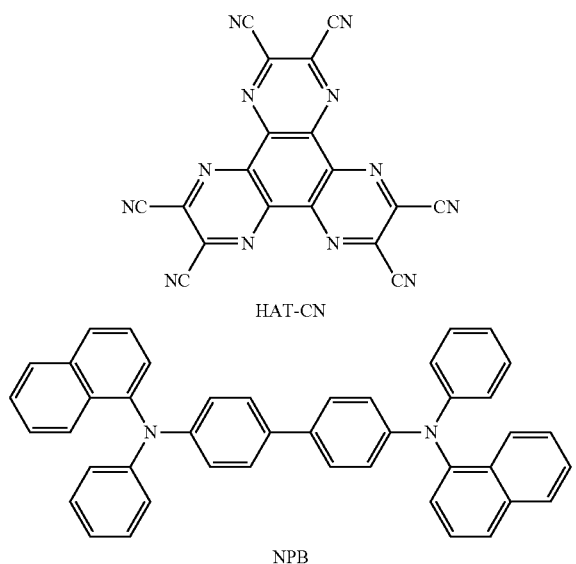
HAT-CN

NPB

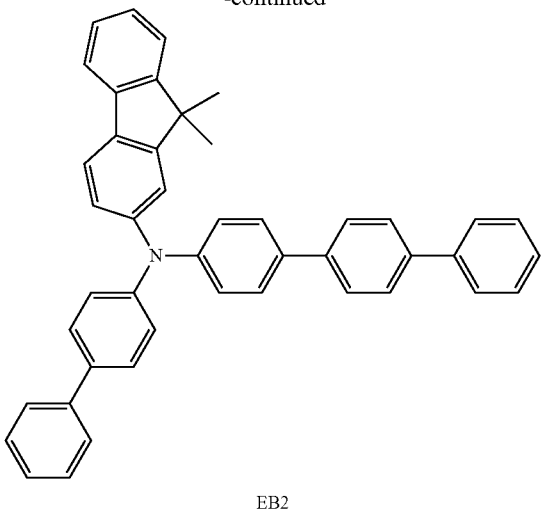
EB2

In the present invention the phosphorescent emitting host used as the following formulas for comparable with EX1 to EX4:

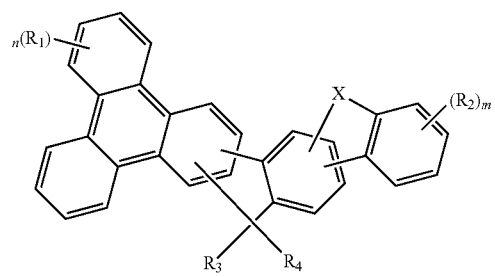

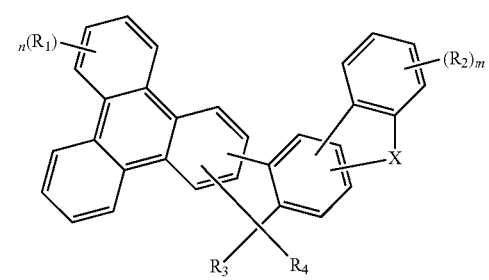

wherein X is a divalent bridge selected from the atom or group consisting from O, S, C(R$_8$)$_2$, N(R$_9$) and Si(R$_{10}$)$_2$, m represents an integer of 0 to 4, n represents an integer of 0 to 8, R$_1$ to R$_4$ and R$_8$ to R$_{10}$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms; wherein the phosphorescent light emitting host is selected from the group consisting of:

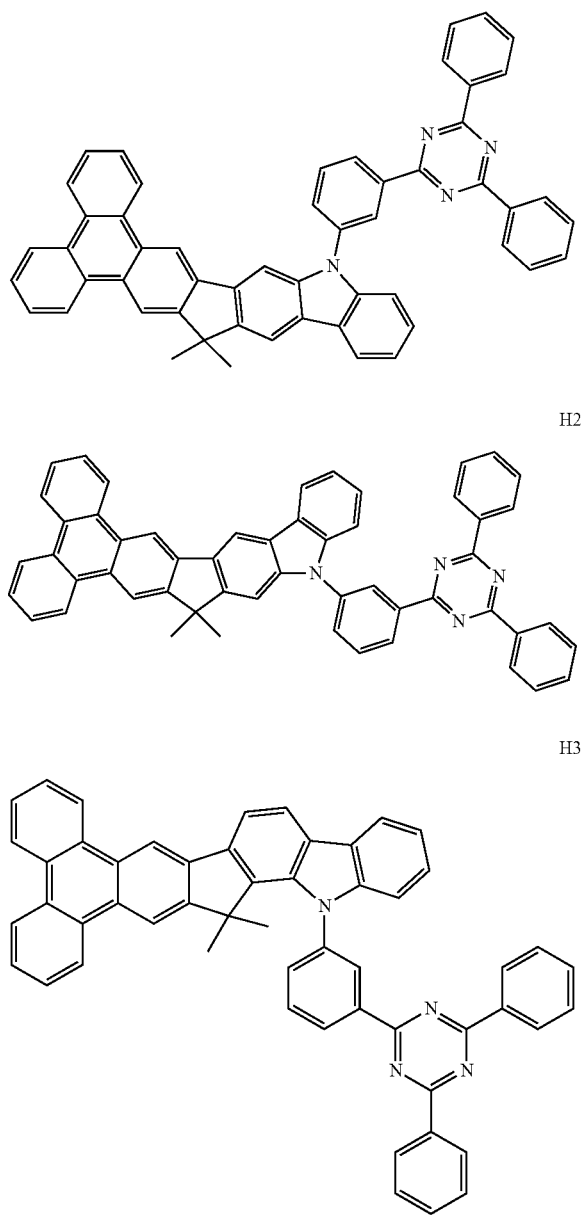
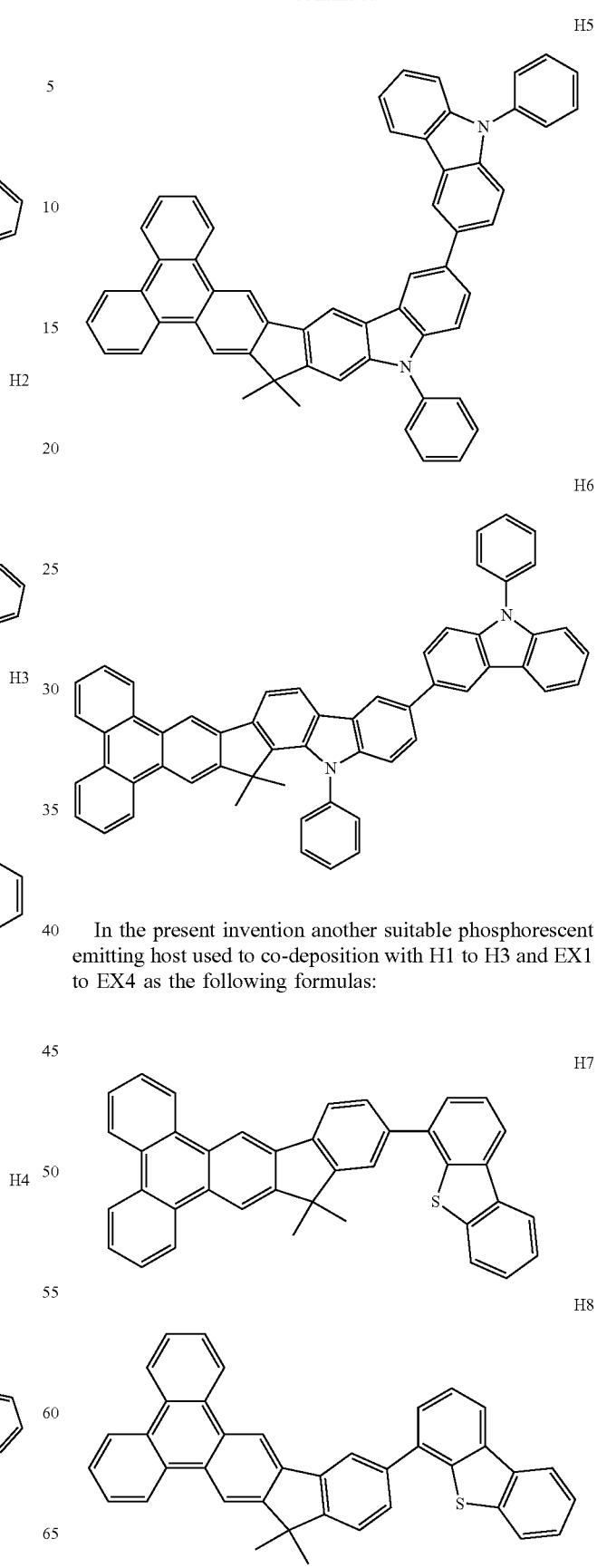
In the present invention another suitable phosphorescent emitting host used to co-deposition with H1 to H3 and EX1 to EX4 as the following formulas:

EX1
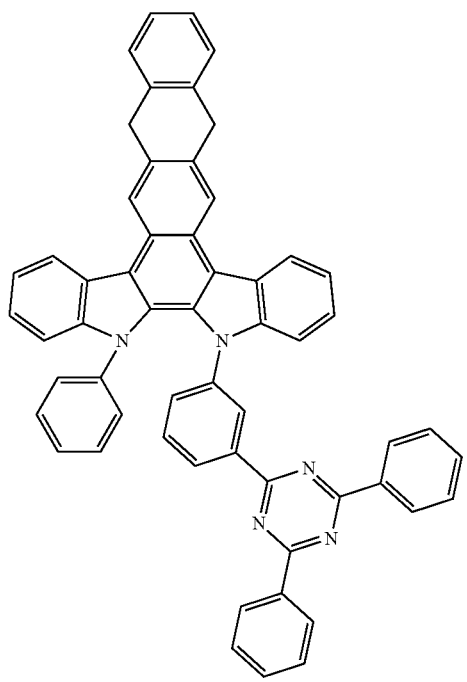
EX2
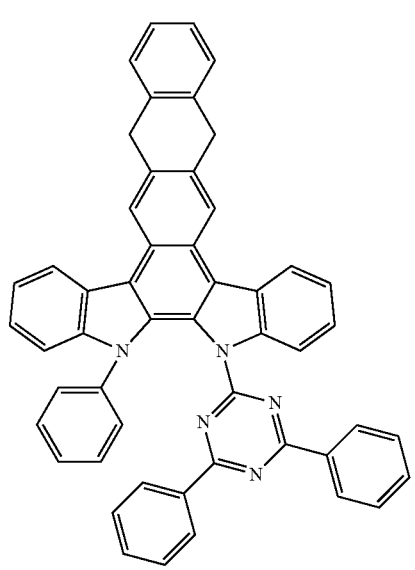
EX3
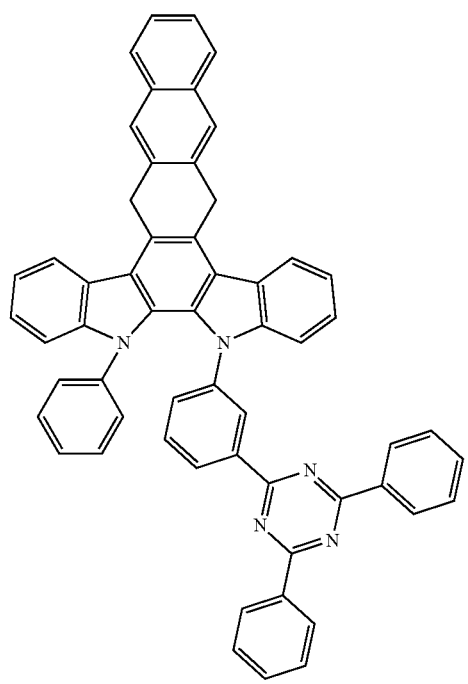
EX4
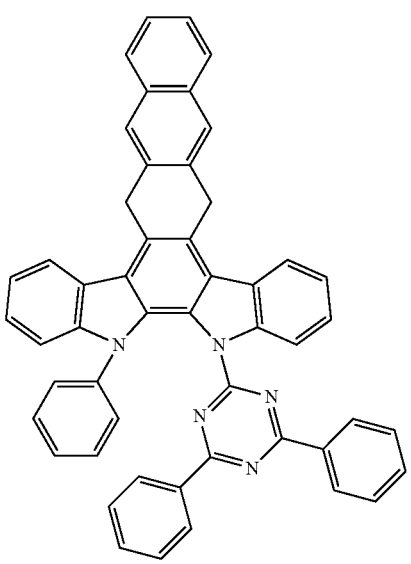
1,3-di(9H-carbazol-9-yl)benzene(mCP) is used as delayed fluorescence host for light emitting layer, and doped with EX1 to EX4 for organic EL device in the present invention.

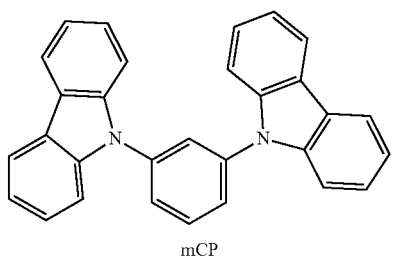 [SMILES: c1cc(-n2c3ccccc3c3ccccc32)cc(-n2c3ccccc3c3ccccc32)c1]

mCP

Organic iridium complexes are widely used as phosphorescent dopant for light emitting layer, and Ir(ppy)₃ is widely used for phosphorescent dopant of light emitting layer for doping in phosphorescent emitting host in the present invention.

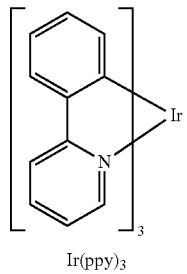

Ir(ppy)₃

HB3 (see the following chemical structure) is used as hole blocking material (HBM) and 2-(10,10-dimethyl-10H-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The prior art of other OLED materials for producing standard organic EL device control and comparable material in this invention shown its chemical structure as follows:

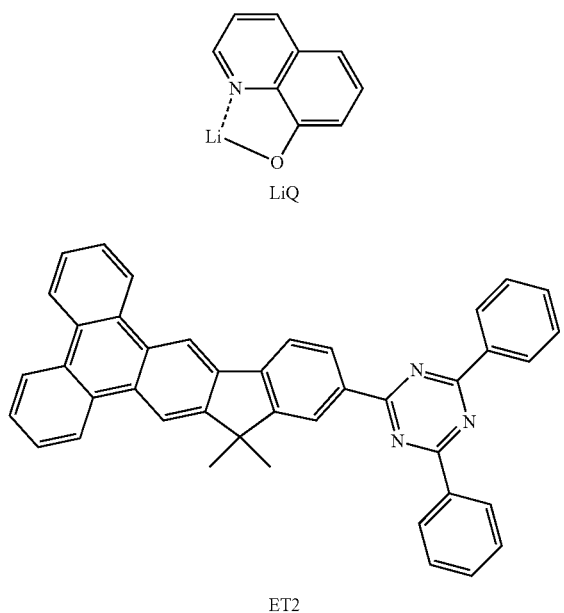

LiQ

ET2

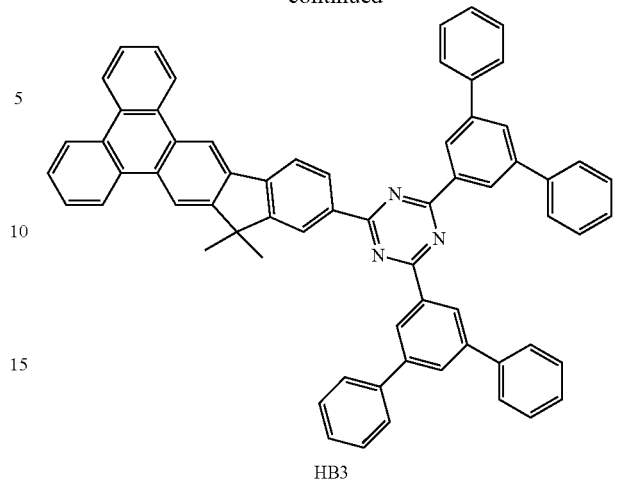

HB3

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or Li₂O. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 5

Using a procedure analogous to the above mentioned general method, phosphorescent emitting organic EL device having the following device structure was produced (See the FIGURE). Device: ITO/HAT-CN (20 nm)/NPB (110 nm)/EB2 (5 nm)/emitting host doped 12% phosphorescent emitting dopant (30 nm)/HBM (10 nm)/ET2 doped 45% LiQ (35 nm)/LiQ (1 nm)/Al (160 nm), and delayed fluorescence device having the following device structure was produced (See the FIGURE). Device: ITO/HAT-CN (20 nm)/NPB (110 nm)/EB2 (5 nm)/mCP doped 25% EX1 to EX4 (25 nm)/HBM (10 nm)/ET2 doped 45% LiQ (35 nm)/LiQ (1 nm)/Al (160 nm). (HBM=hole blocking material) The I—V-B (at 1000 nits) and half-life time of phosphorescent emitting organic EL device testing report as Table 1. The T70 is defined that the initial luminance of 3000 cd/m² has dropped to 2100 cd/m².

TABLE 1

| Emitting host | Emitting dopant | HBM | Voltage (V) | Efficiency (cd/A) | Color | $T_{70}$ |
|---|---|---|---|---|---|---|
| EX1 | Ir(ppy)₃ | HB3 | 4.0 | 35 | green | 430 |
| EX2 | Ir(ppy)₃ | HB3 | 4.7 | 32 | green | 320 |
| EX3 | Ir(ppy)₃ | HB3 | 4.5 | 38 | green | 440 |
| EX4 | Ir(ppy)₃ | HB3 | 4.9 | 41 | green | 310 |

TABLE 1-continued

| Emitting host | Emitting dopant | HBM | Voltage (V) | Efficiency (cd/A) | Color | $T_{70}$ |
| --- | --- | --- | --- | --- | --- | --- |
| H1 | Ir(ppy)$_3$ | HB3 | 4.8 | 32 | green | 220 |
| H2 | Ir(ppy)$_3$ | HB3 | 4.3 | 31 | green | 250 |
| H3 | Ir(ppy)$_3$ | HB3 | 4.5 | 22 | green | 150 |
| EX1 + H8 | Ir(ppy)$_3$ | HB3 | 3.6 | 52 | green | 330 |
| H3 + H8 | Ir(ppy)$_3$ | HB3 | 3.5 | 45 | green | 350 |
| H3 + H6 | Ir(ppy)$_3$ | HB3 | 3.2 | 50 | green | 550 |
| EX4 + H7 | Ir(ppy)$_3$ | HB3 | 3.0 | 55 | green | 580 |
| EX4 + H7 | Ir(ppy)$_3$ | EX1 | 4.3 | 45 | green | 230 |
| EX4 + H7 | Ir(ppy)$_3$ | EX2 | 4.6 | 35 | green | 350 |
| EX4 + H7 | Ir(ppy)$_3$ | EX3 | 4.5 | 50 | green | 380 |
| EX4 + H7 | Ir(ppy)$_3$ | EX4 | 4.0 | 47 | green | 260 |
| mCP | EX1 | HB3 | 5.0 | 21 | green | 80 |
| mCP | EX2 | HB3 | 5.0 | 26 | green | 65 |
| mCP | EX3 | HB3 | 5.3 | 18 | green | 70 |
| mCP | EX4 | HB3 | 4.8 | 31 | green | 25 |

In the above preferred embodiments for organic EL device test report (see Table 1), we shown that the material with a general formula(1) or formula(2) used as phosphorescent emitting host in the present invention display good performance than the prior art of OLED materials. Additional, EX1 to EX4 used as delayed fluorescence dopant to co-deposit with mCP can show good efficiency reach to 30 cd/A.

To sum up, the present invention discloses a material which can be used for organic EL device is disclosed. More specifically, an organic EL device employing the material as phosphorescent emitting host, delayed fluorescence dopant, and hole blocking layer (HBL). The mentioned the material is represented by the following formula(1) or formula(2):

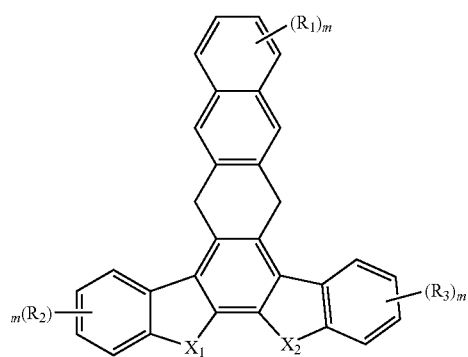

formula(1)

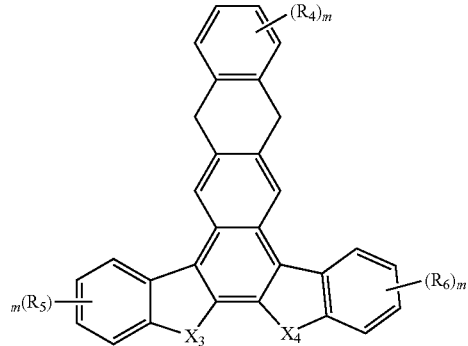

formula(2)

wherein m represents an integer of 0 to 4, $X_1$ to $X_4$ independently represent a divalent bridge selected from the atom or group consisting from O, S, C($R_7$)($R_8$), N(Ar), Si($R_9$)($R_{10}$), Ar is selected from the group consisting of a hydrogen, a substituted or unsubstituted aryl group having 6 to 60 carbon atoms or a substituted or unsubstituted heteroaryl group having 3 to 60 carbon atoms, and provided that Ar represents a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted quinoline group, a substituted or unsubstituted isoquinoline group, a substituted or unsubstituted quinazoline group, a substituted or unsubstituted phenanthroline group, a substituted or unsubstituted dihydroacridine group, a substituted or unsubstituted phenothiazine group, a substituted or unsubstituted phenoxazine group, and a substituted or unsubstituted dihydrophenazine group; $R_1$ to $R_{10}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:
1. A material with a general formula(1) or formula(2) as follows:

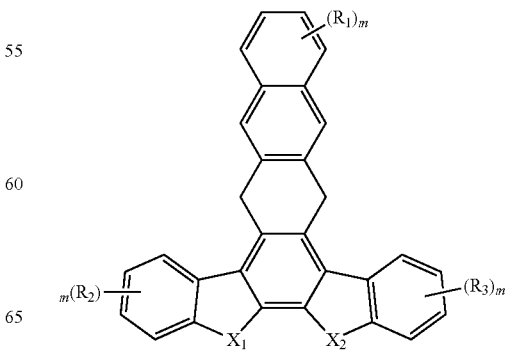

formula (1)

formula (2)

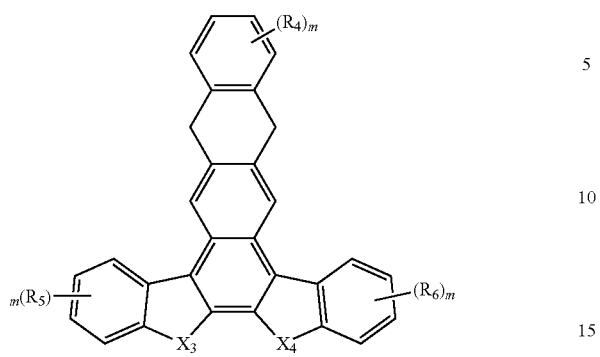

wherein m represents an integer of 0 to 4, $X_1$ to $X_4$ independently represent a divalent bridge selected from the atom or group consisting from O, S, $C(R_7)(R_8)$, $N(Ar)$, $Si(R_9)(R_{10})$, Ar is selected from the group consisting of a hydrogen, a substituted or unsubstituted aryl group having 6 to 60 carbon atoms or a substituted or unsubstituted heteroaryl group having 3 to 60 carbon atoms, and provided that when Ar is a substituted or unsubstituted heteroaryl group having 3 to 60 carbon atoms, Ar represents a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted quinoline group, a substituted or unsubstituted isoquinoline group, a substituted or unsubstituted quinazoline group, a substituted or unsubstituted phenanthroline group, a substituted or unsubstituted dihydroacridine group, a substituted or unsubstituted phenothiazine group, a substituted or unsubstituted phenoxazine group, and a substituted or unsubstituted dihydrophenazine group; $R_1$ to $R_{10}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

2. The material according to claim 1, wherein the Ar is represented by the following formula(3) to formula(6):

Formula(3)

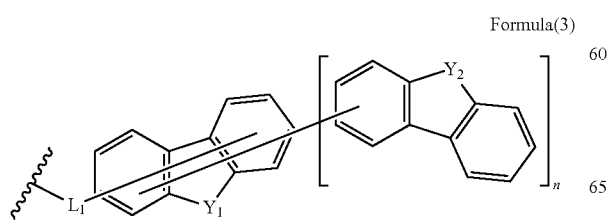

Formula(4)

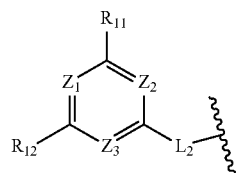

Formula(5)

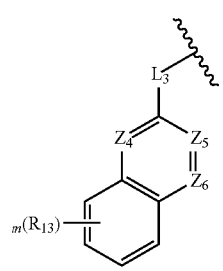

Formula(6)

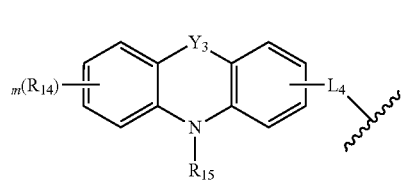

wherein $L_1$ to $L_4$ represent a single bond, a substituted or unsubstituted arylene group having 6 to 30 ring carbon atoms, or a substituted or unsubstituted heterarylene group having 3 to 30 ring carbon atoms, m represents an integer of 0 to 4, n represents an integer of 0 or 1, $Y_1$ to $Y_3$ independently represent a divalent bridge selected from the atom or group consisting from O, S, $C(R_{16})(R_{17})$, $N(R_{18})$, $Z_1$ to $Z_6$ represent a nitrogen atom or $C(R_s)$, and each $R_s$ represents a hydrogen, a phenyl, a substituted or unsubstituted alkyl group having 1 to 30 carbon atoms, and a substituted or unsubstituted aryl group having 6 to 30 carbon atoms; $R_{11}$ to $R_{18}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

3. The material according to claim 1, wherein the material is selected from the group consisting of:

67
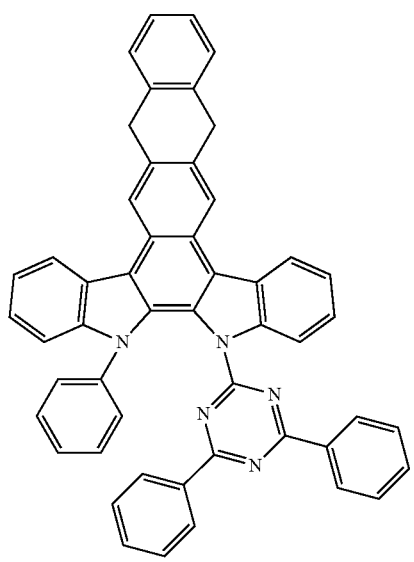
68
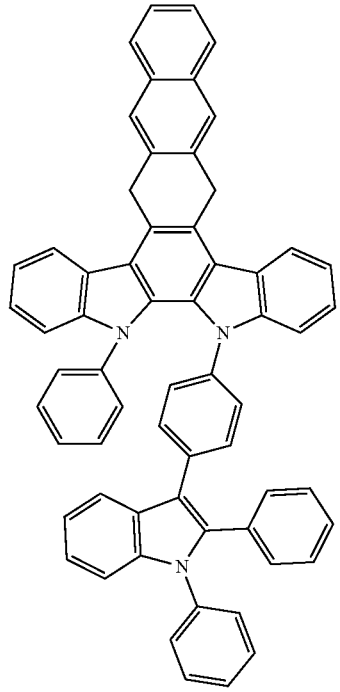
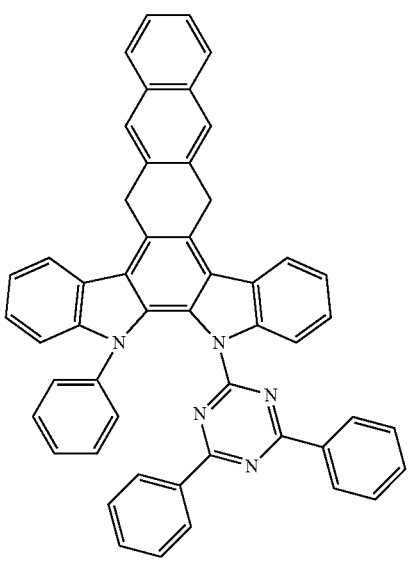

69
-continued
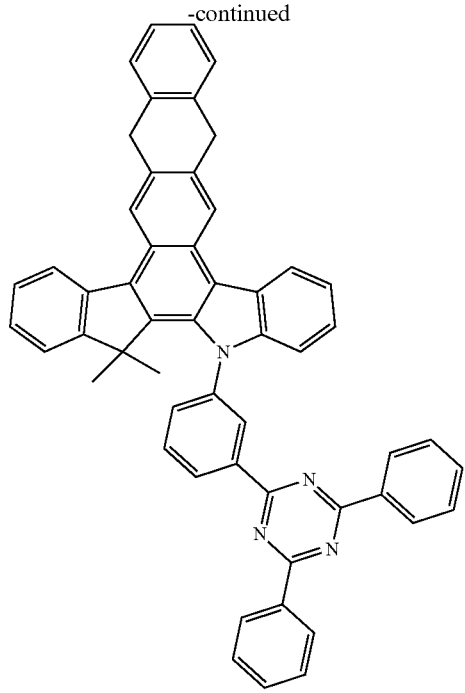
70
-continued
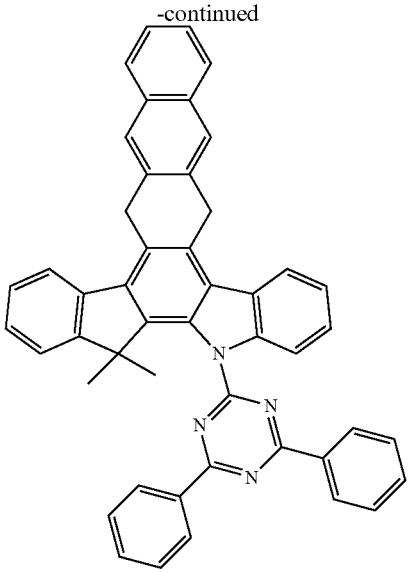
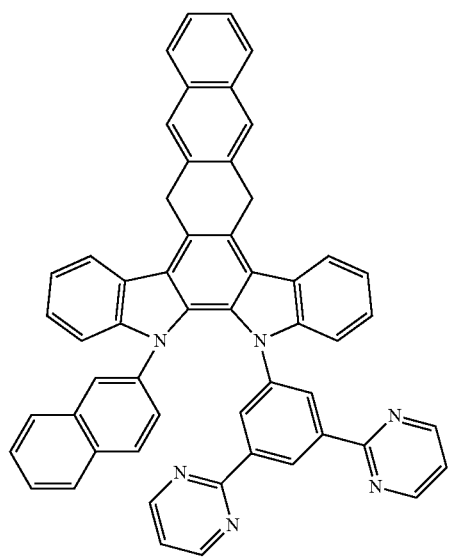
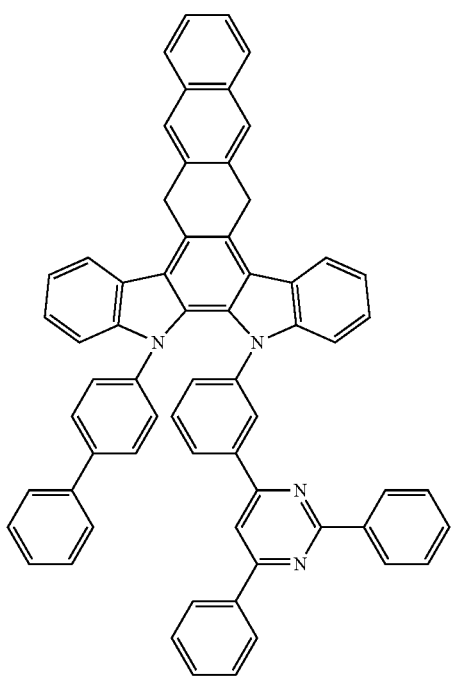

-continued
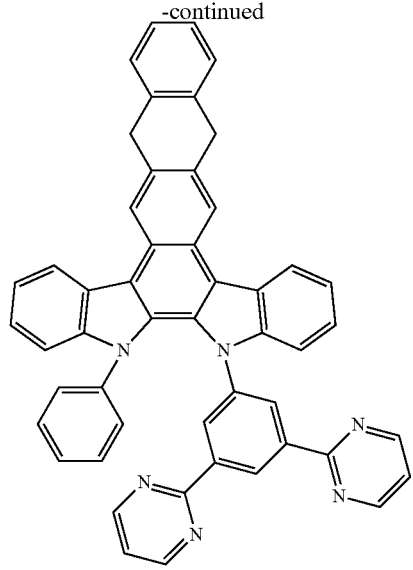
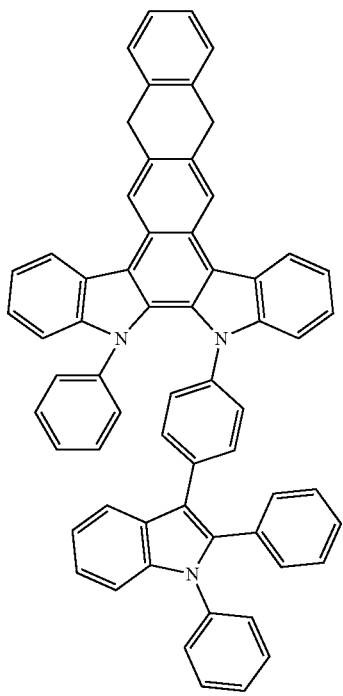
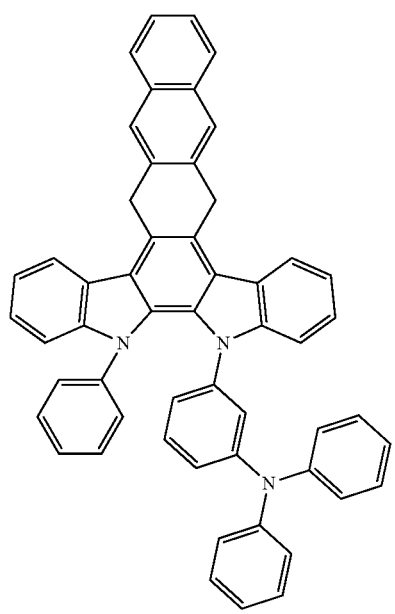

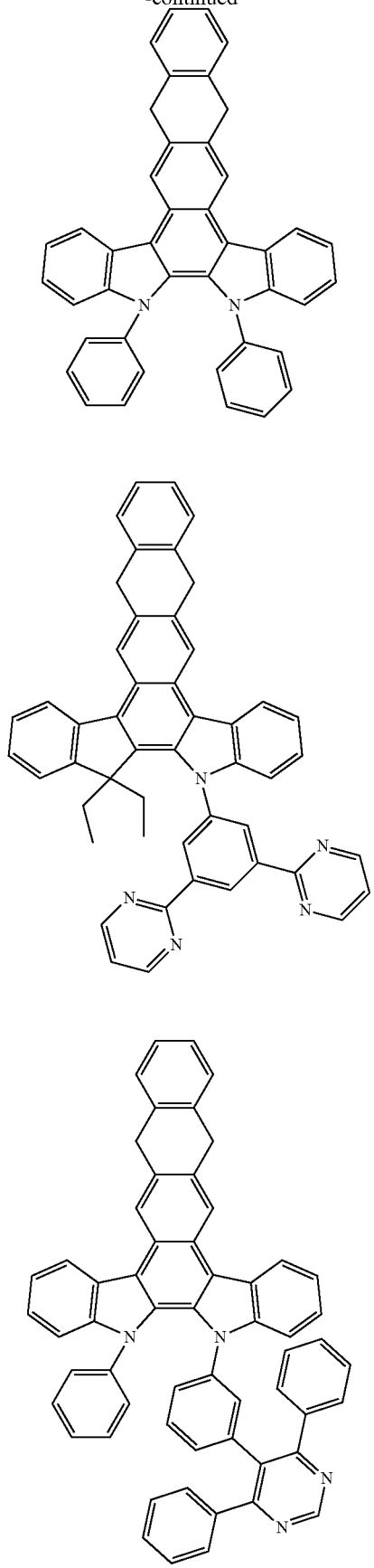
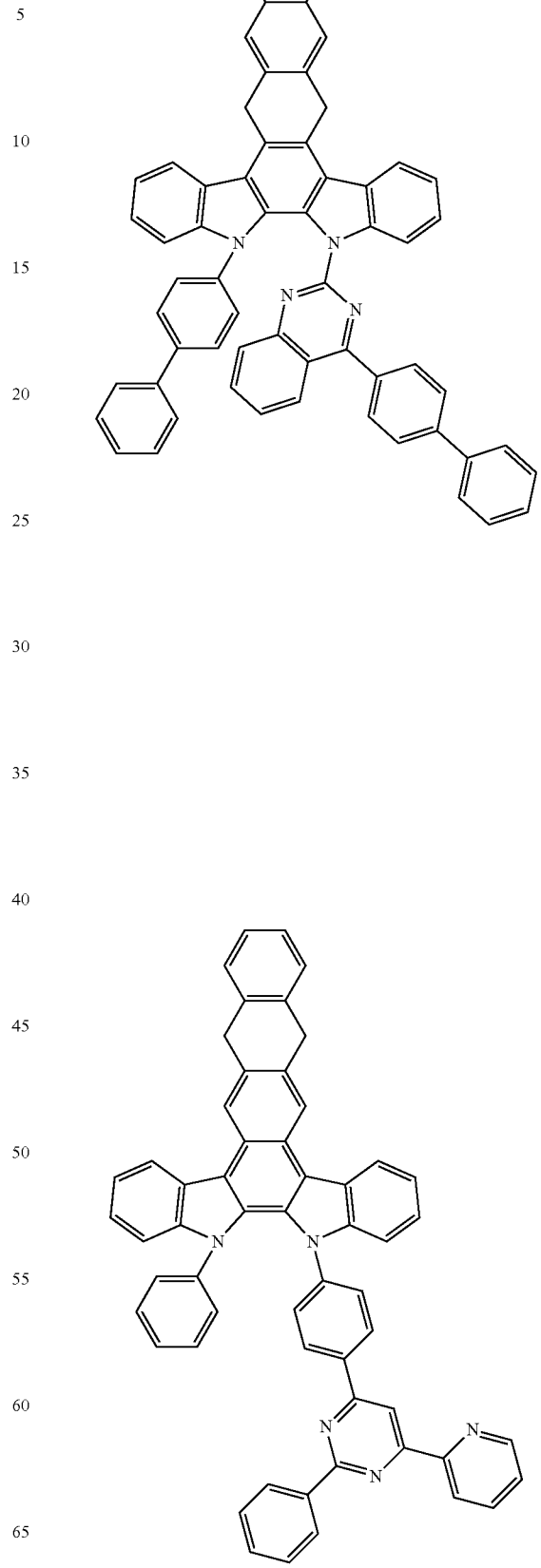

75
-continued
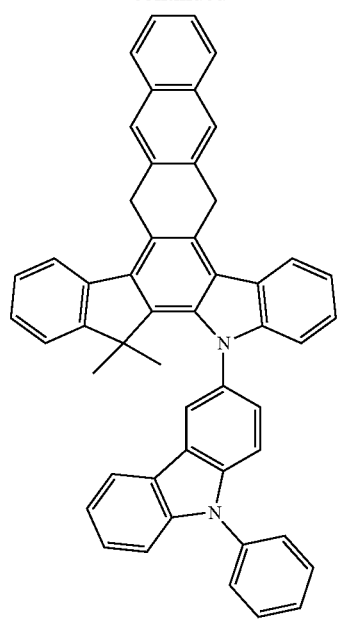
76
-continued
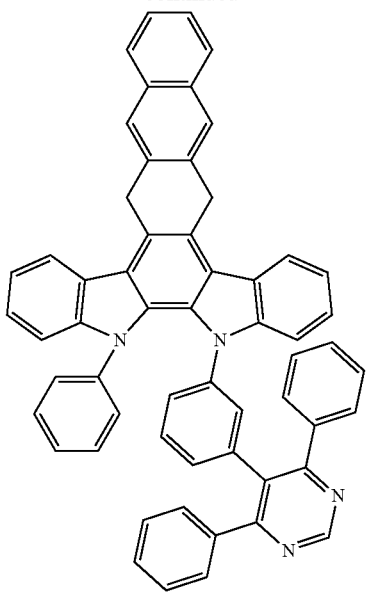
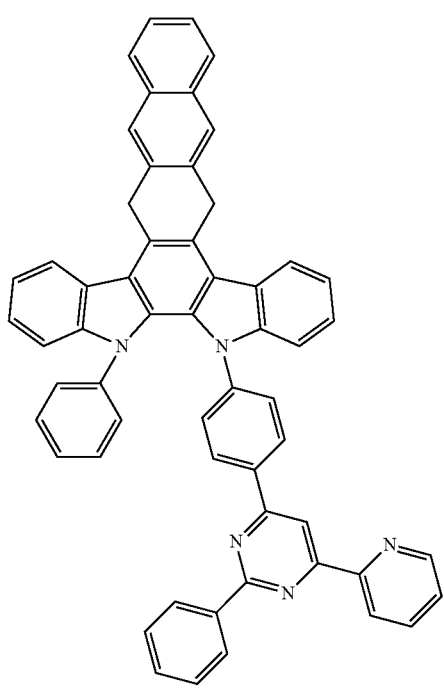
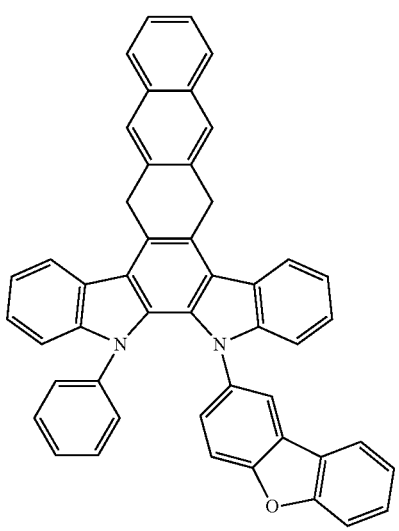

77
-continued
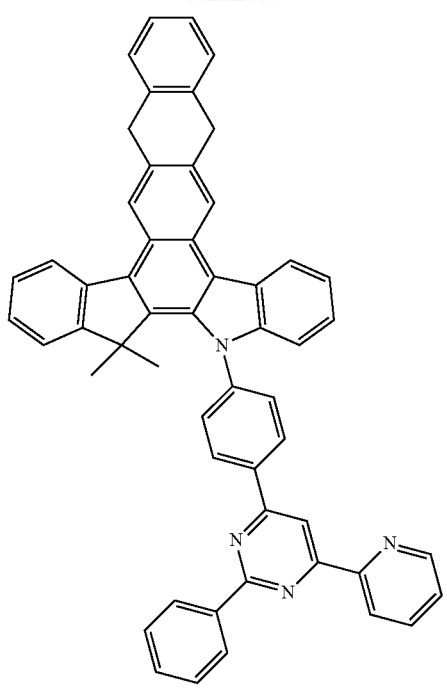
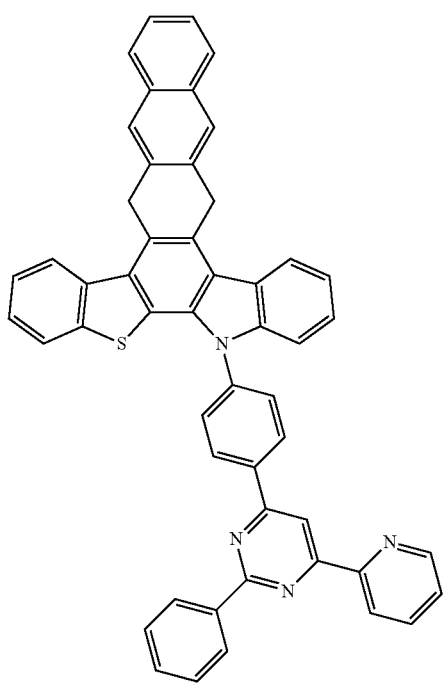
78
-continued
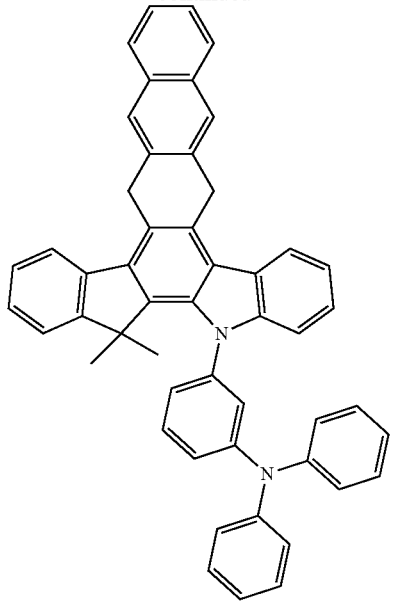
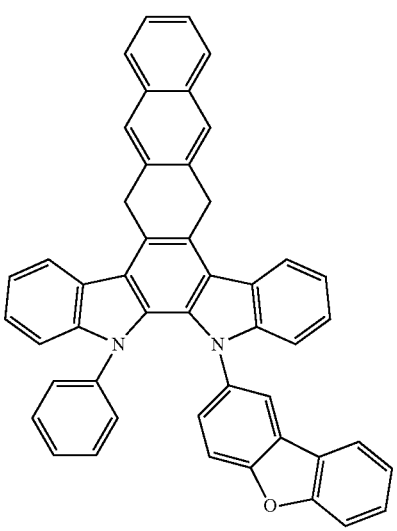

79
-continued
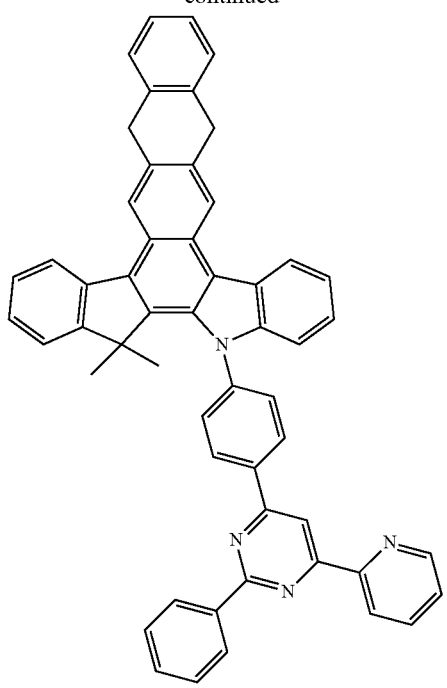
80
-continued
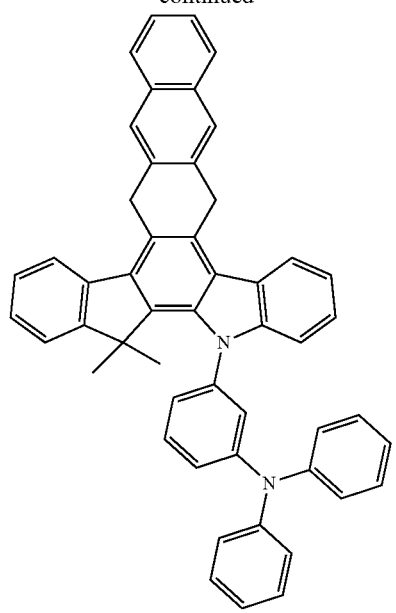
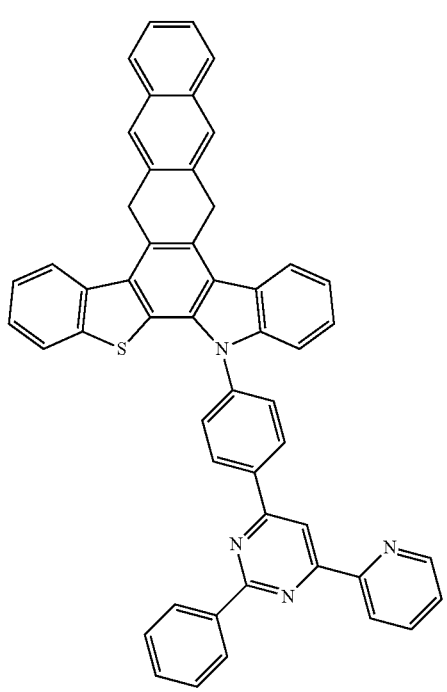
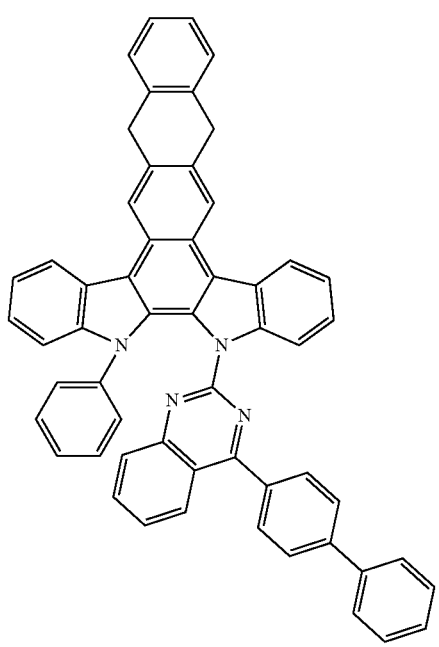

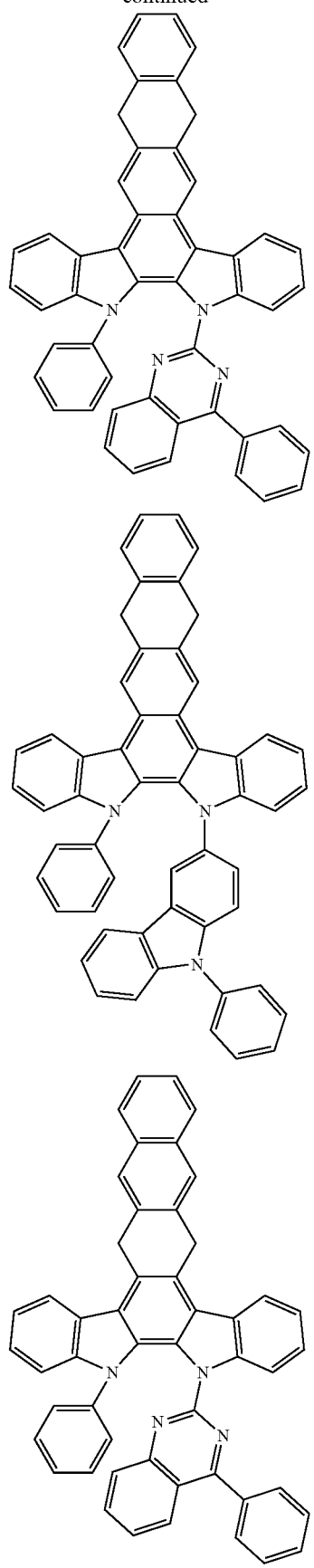

83
-continued
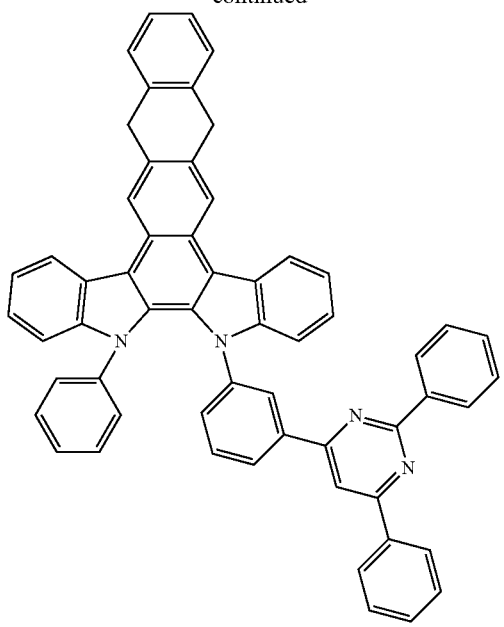
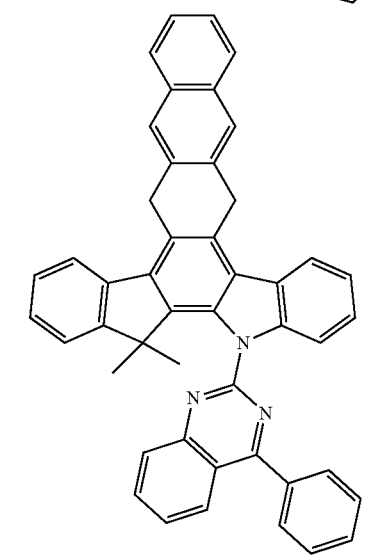
84
-continued
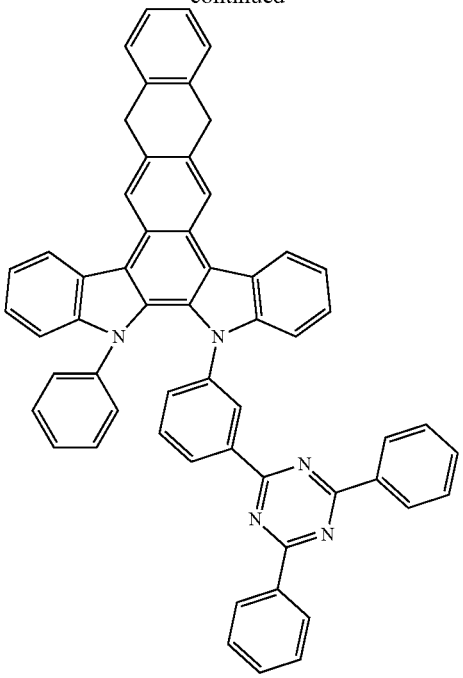
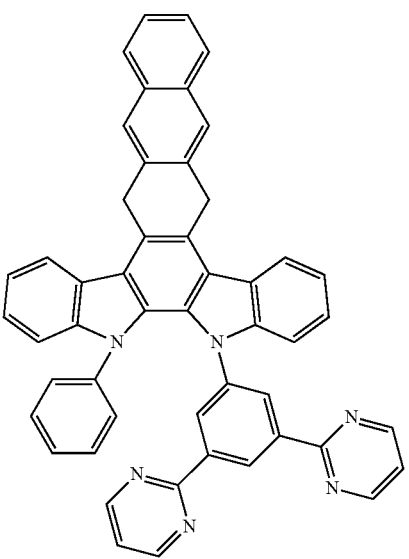

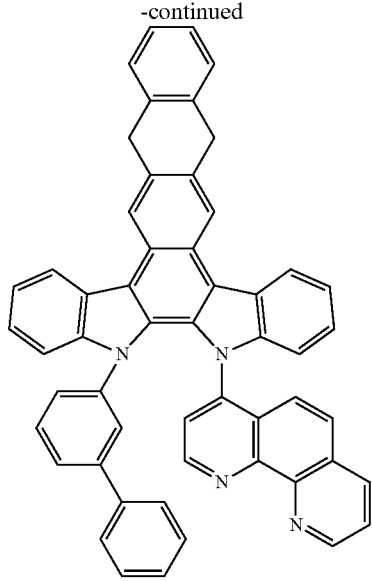
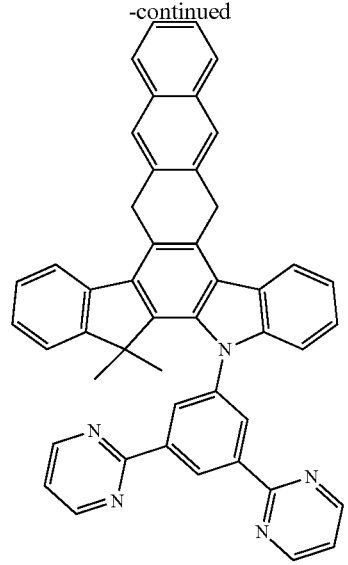
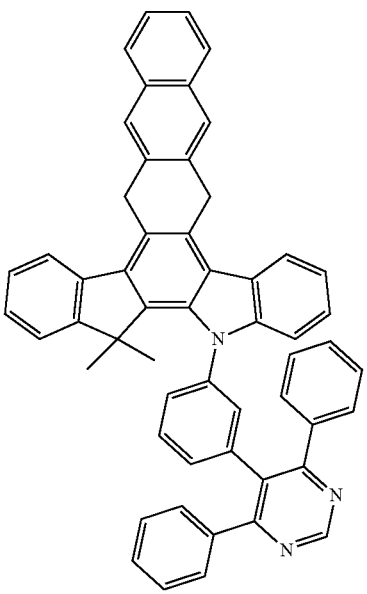
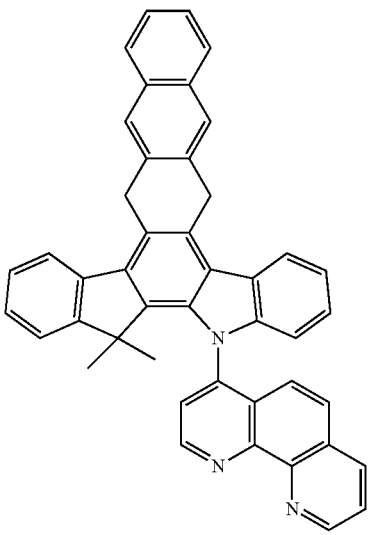

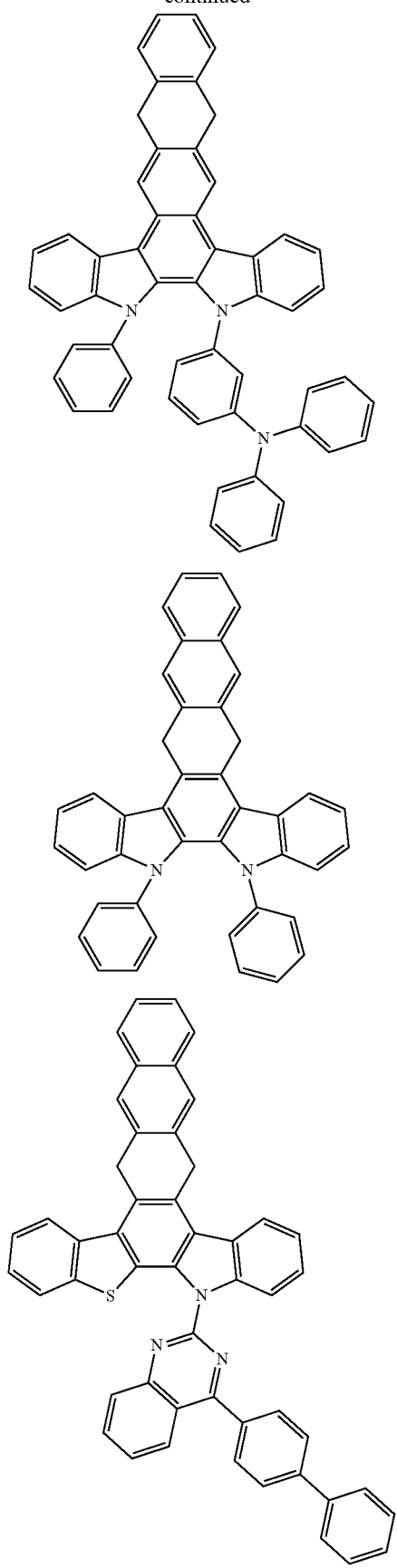
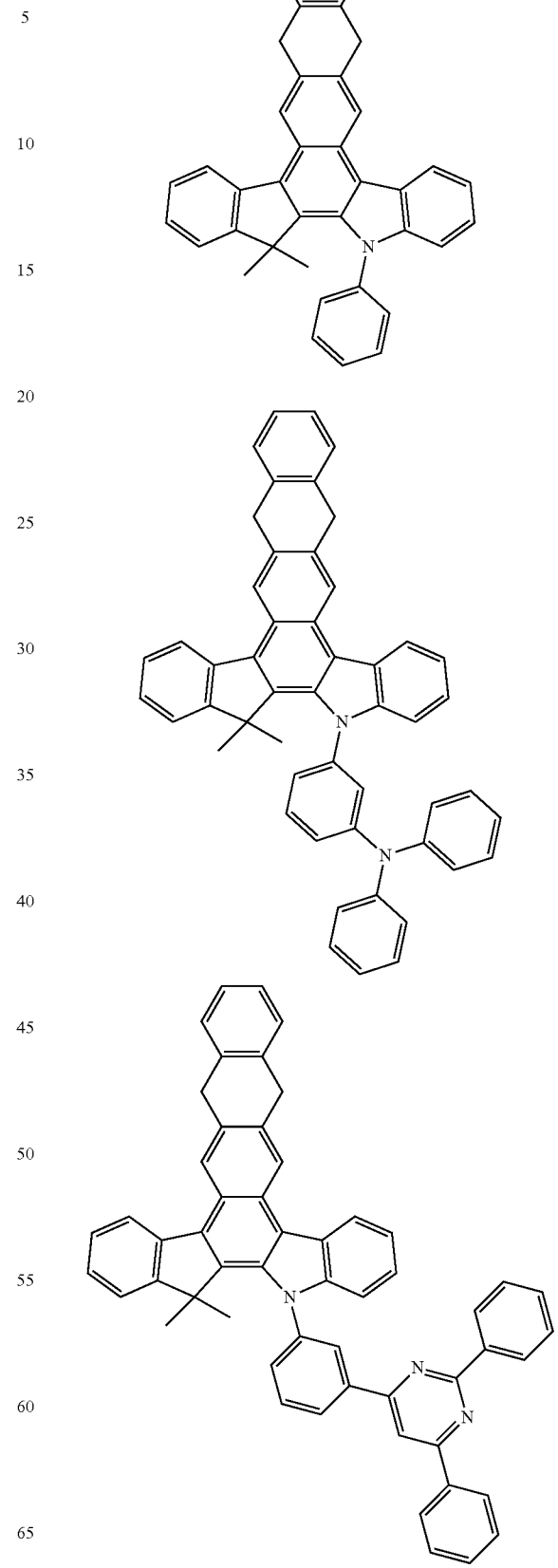

89
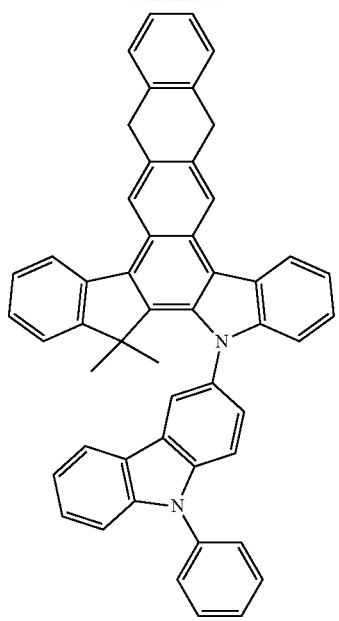
90
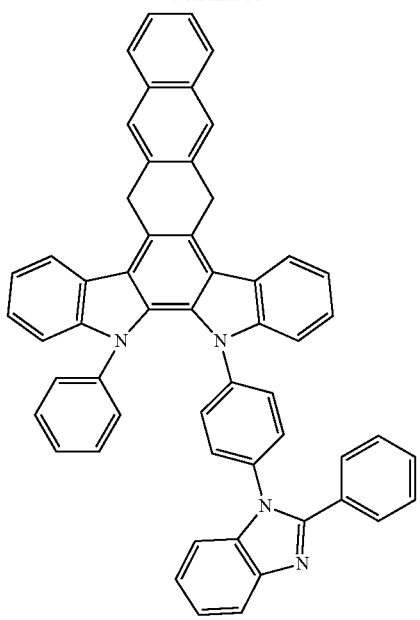
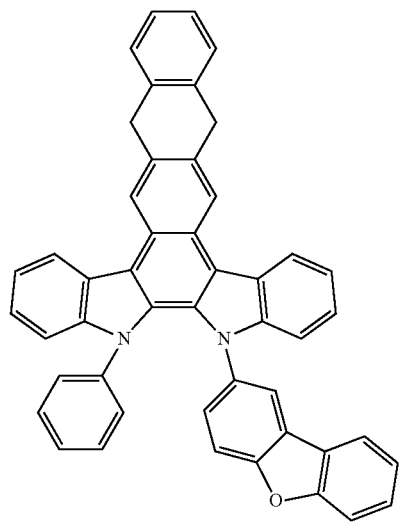
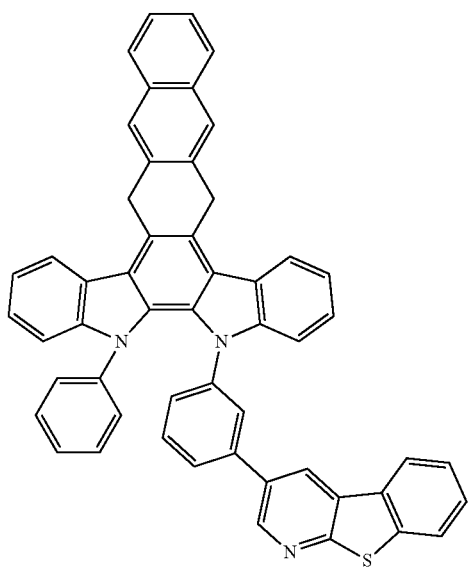

91
-continued
92
-continued
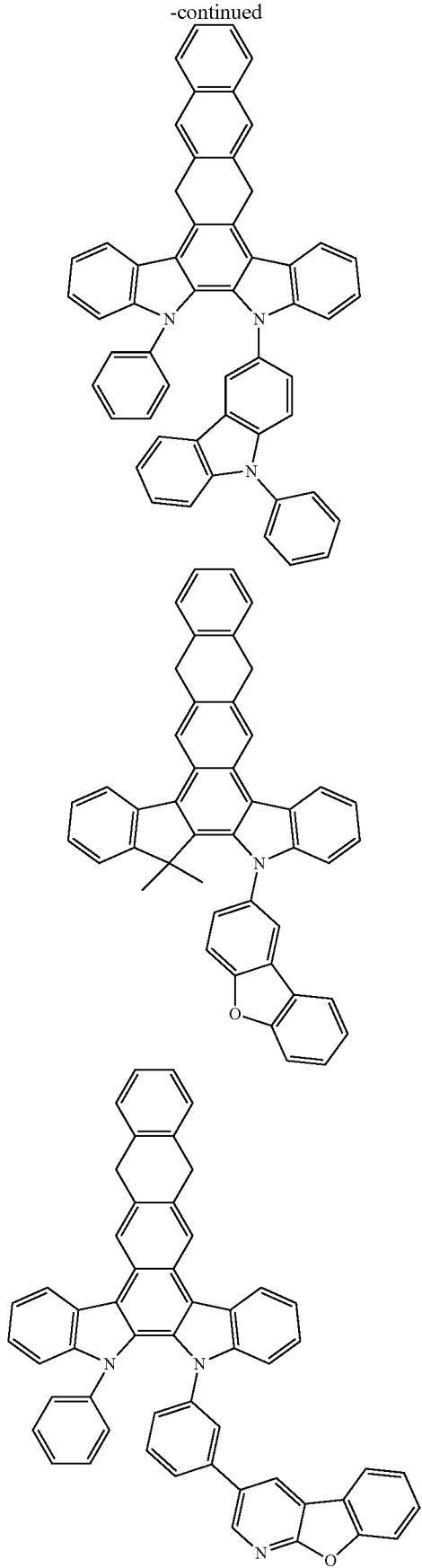
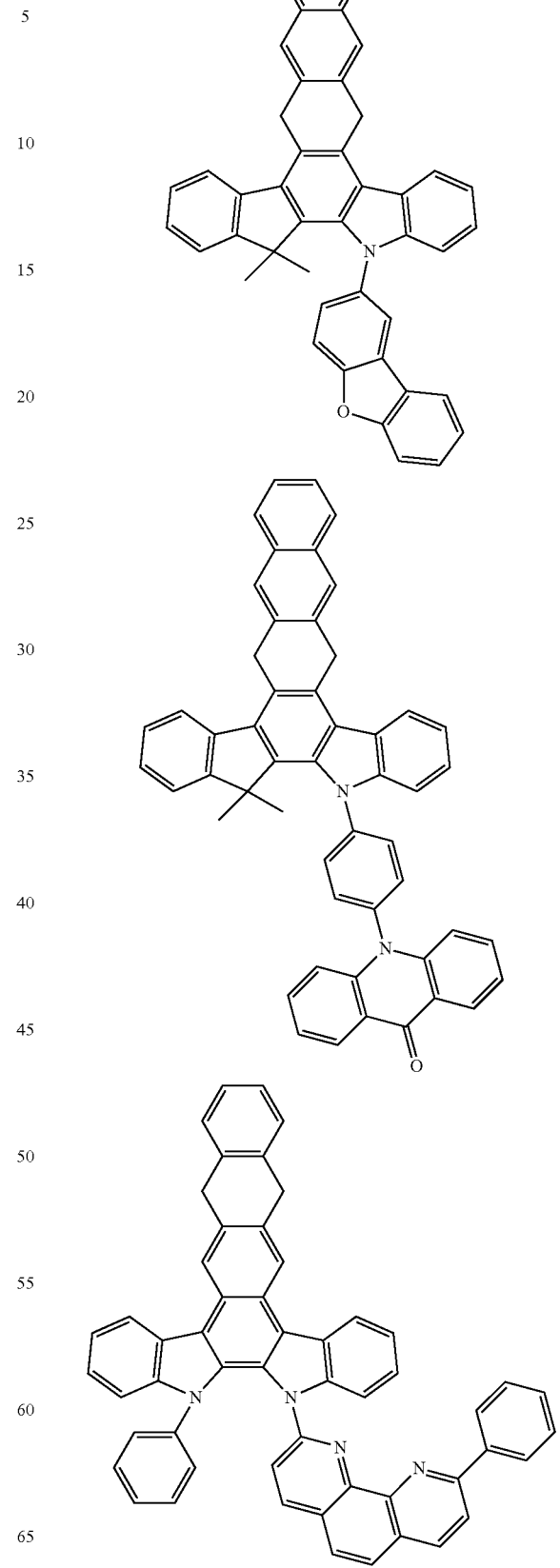

93
-continued
94
-continued
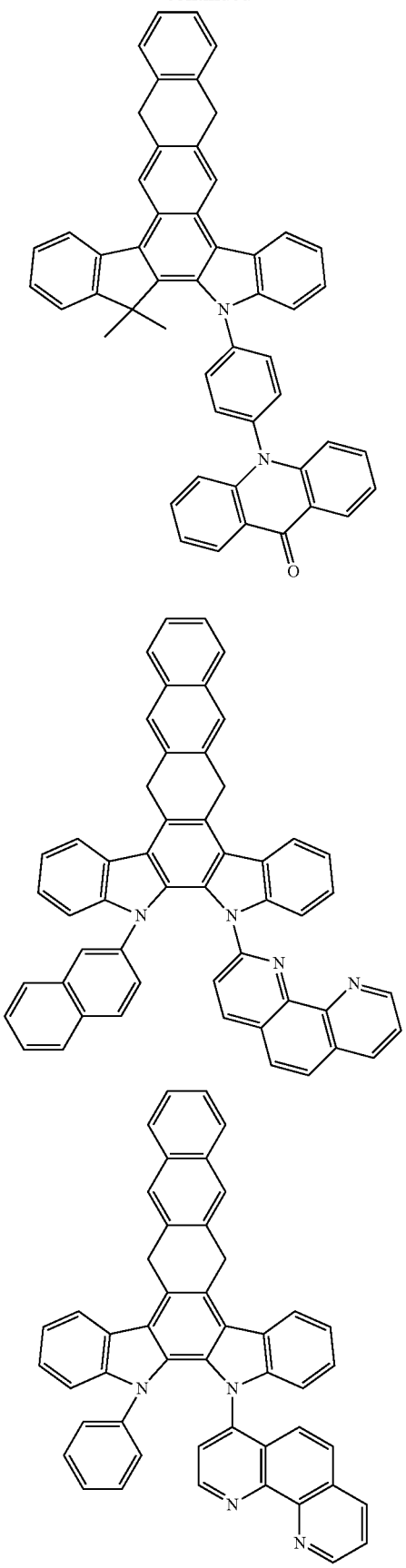
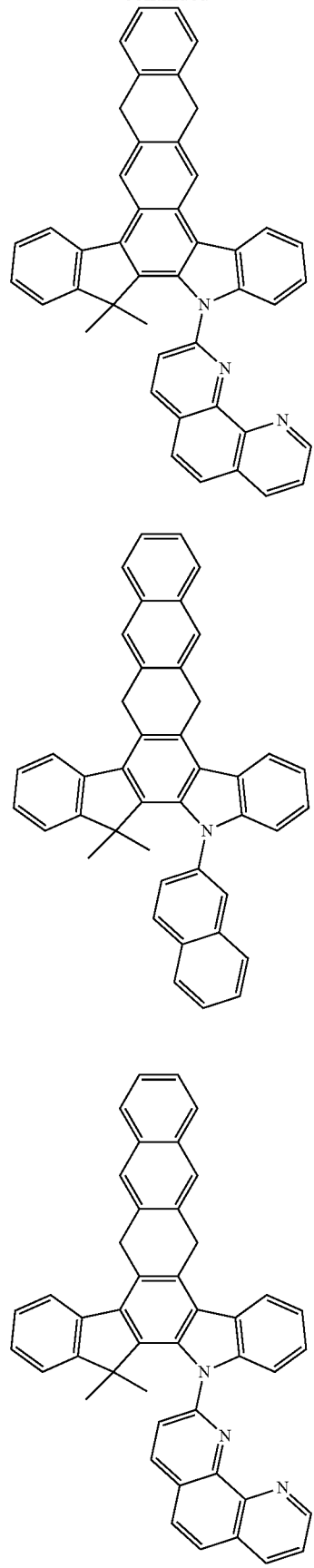

95
-continued
96
-continued
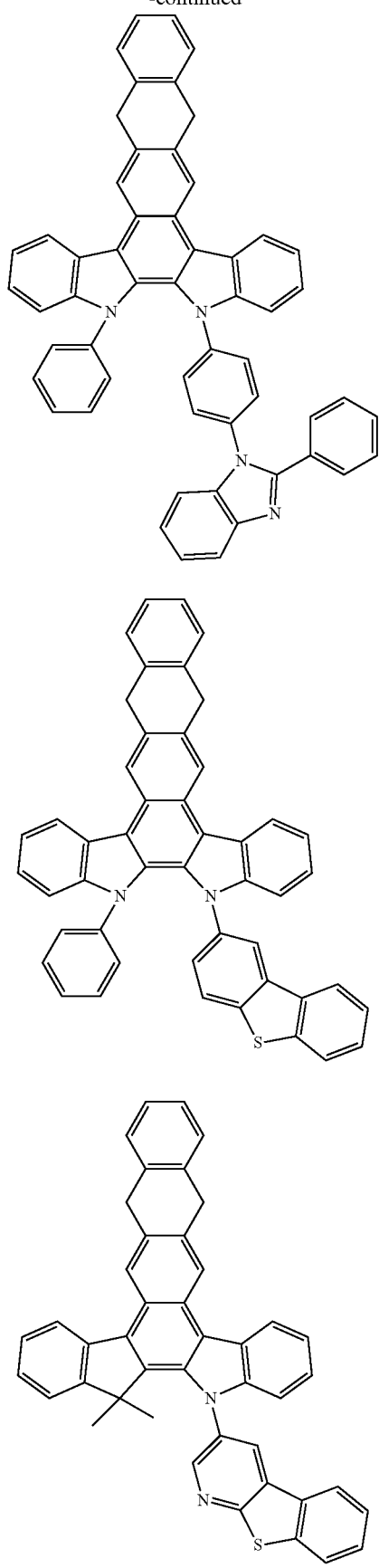
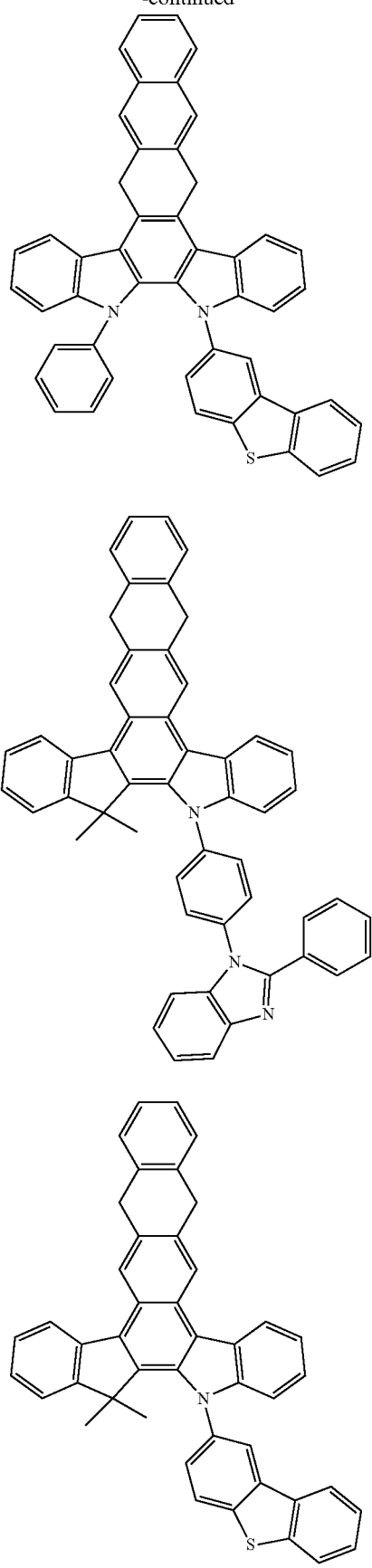

97
-continued
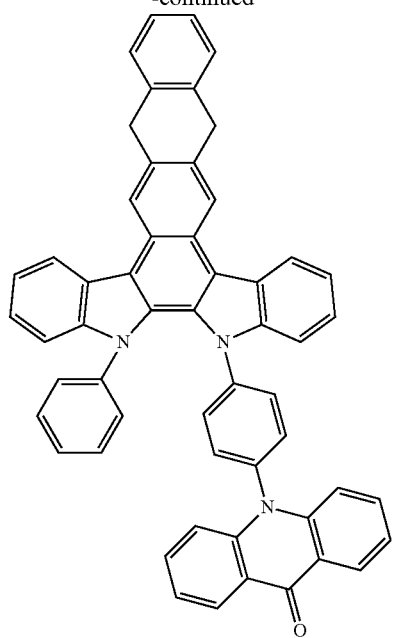
98
-continued
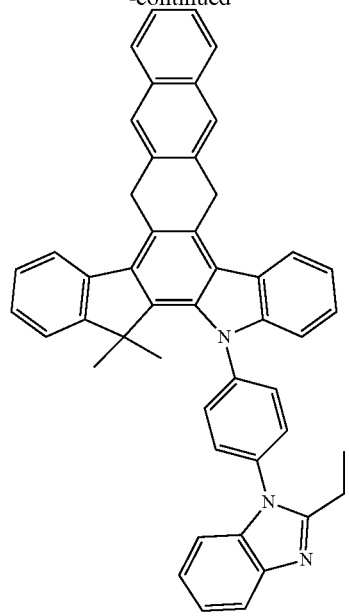
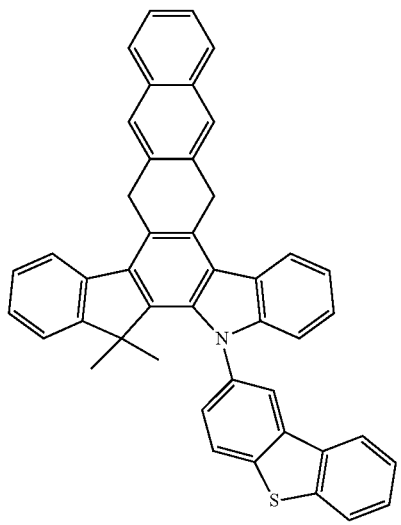
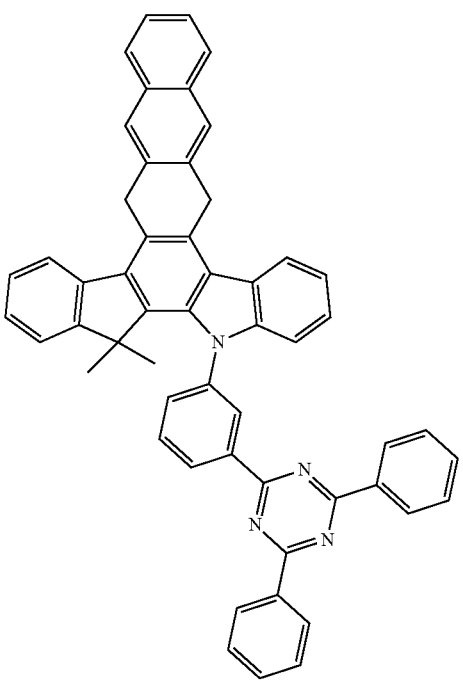

99
-continued
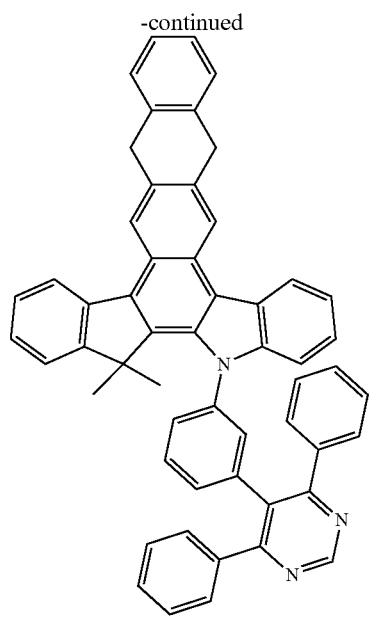
100
-continued
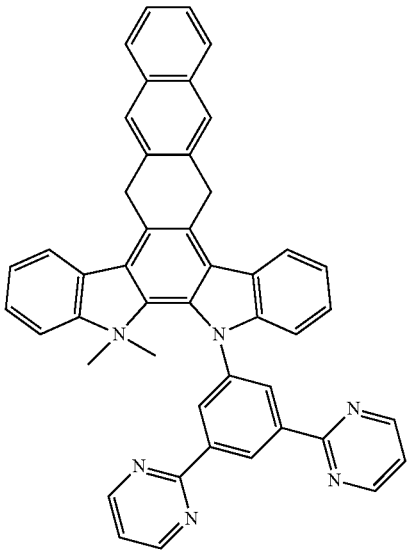
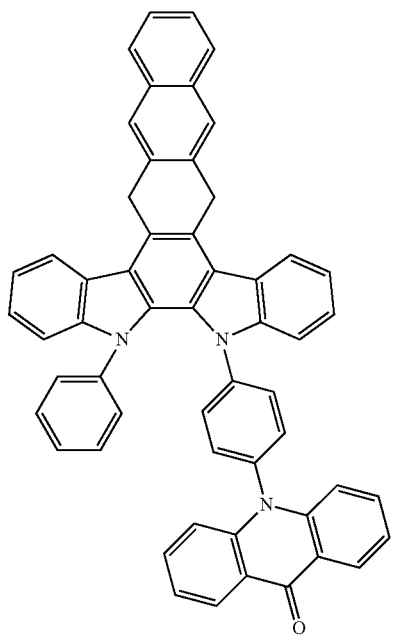
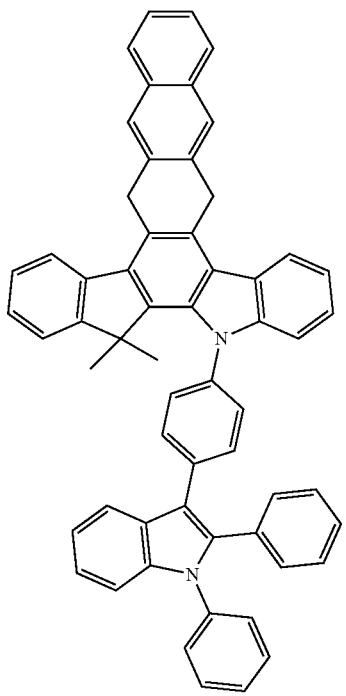

101
-continued
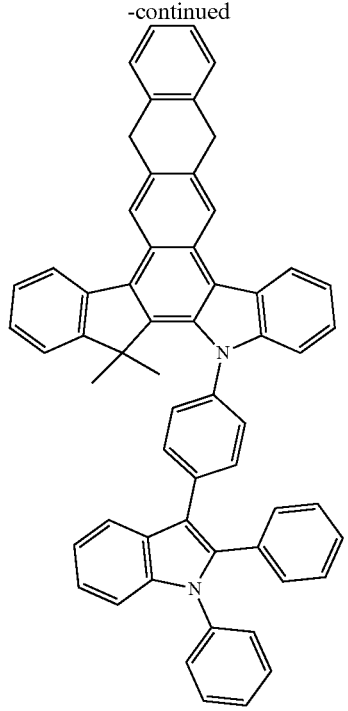
102
-continued
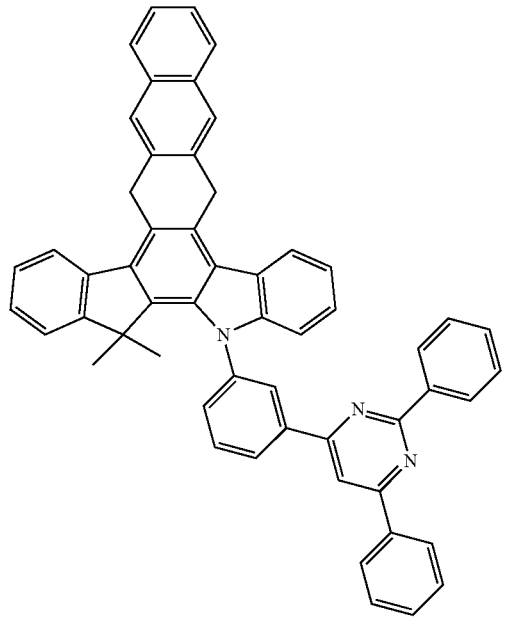
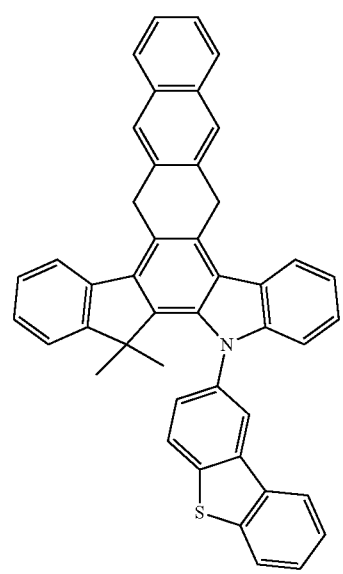
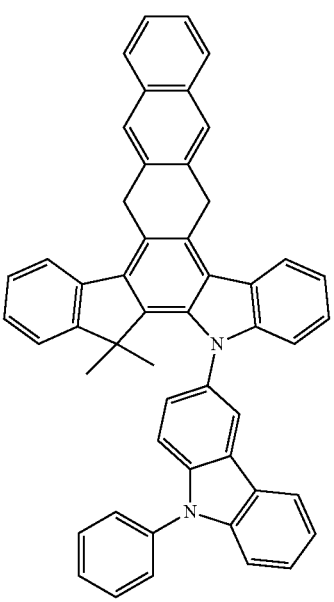

-continued

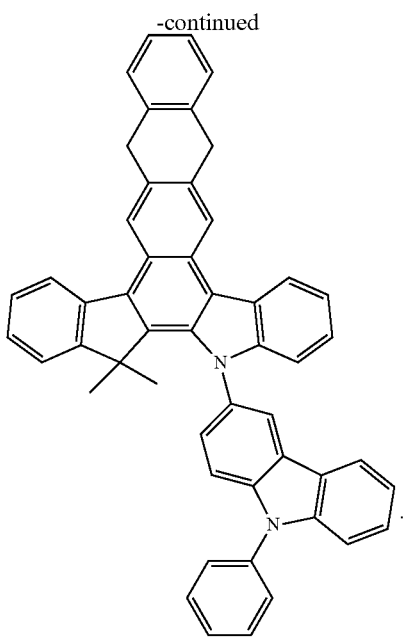

4. A organic electroluminescence device comprising a pair of electrodes consisting of a cathode and an anode, and between the pairs of electrodes comprising at least a light emitting layer, one or more layers of organic thin film layer, wherein the light emitting layer or the organic thin film layer comprising the material according to claim 1.

5. The organic electroluminescence device according to claim 4, wherein the light emitting layer comprising the material with a general formula(1) or formula(2) is a phosphoescent host material.

6. The organic electroluminescence device according to claim 4, wherein the light emitting layer comprising the material with a general formula(1) or formula(2) is a thermally activated delayed fluorescence host material.

7. The organic electroluminescence device according to claim 4, wherein the light emitting layer comprising the material with a general formula(1) or formula(2) is a thermally activated delayed fluorescence dopant material.

8. The organic electroluminescence device according to claim 4, wherein the organic thin film layer comprising the material with a general formula(1) or formula(2) is a hole blocking material.

9. The organic electroluminescence device according to claim 4, wherein the organic thin film layer comprising the material with a general f formula(1) or formula(2) is an electron transport material.

10. The organic electroluminescence device according to claim 4, wherein the light emitting layer emits phosphorescent red, blue, green and yellow lights.

11. The organic electroluminescence device according to claim 4, wherein the light emitting layer emits thermally activated delayed fluorescent red, blue, green and yellow lights.

12. The organic electroluminescence device according to claim 4, wherein the device is an organic light emitting device.

13. The organic electroluminescent device according to claim 4, wherein the device is a lighting panel.

14. The organic electroluminescent device according to claim 4, wherein the device is a backlight panel.

* * * * *